United States Patent
McKinney et al.

(10) Patent No.: US 11,185,245 B2
(45) Date of Patent: Nov. 30, 2021

(54) CATHETER FOR MONITORING PRESSURE FOR MUSCLE COMPARTMENT SYNDROME

(71) Applicant: Sentinel Medical Technologies, LLC, Boca Raton, FL (US)

(72) Inventors: Timothy McKinney, Boca Raton, FL (US); Marc-Alan Levine, Pottstown, PA (US)

(73) Assignee: Sentinel Medical Technologies, LLC., Boca Raton, FL (US)

( * ) Notice: Subject to any disclaimer, the term of this patent is extended or adjusted under 35 U.S.C. 154(b) by 287 days.

(21) Appl. No.: 15/990,569

(22) Filed: May 25, 2018

(65) Prior Publication Data

US 2018/0344184 A1    Dec. 6, 2018

Related U.S. Application Data

(63) Continuation-in-part of application No. 15/949,005, filed on Apr. 9, 2018.
(Continued)

(51) Int. Cl.
*A61B 5/03* (2006.01)
*A61B 5/00* (2006.01)
(Continued)

(52) U.S. Cl.
CPC ............ *A61B 5/036* (2013.01); *A61B 5/4519* (2013.01); *A61B 5/6853* (2013.01); *A61B 5/14551* (2013.01); *A61B 5/6812* (2013.01); *A61B 5/742* (2013.01); *A61B 2562/028* (2013.01); *A61B 2562/0247* (2013.01); *A61M 25/0032* (2013.01); *A61M 25/10* (2013.01); *A61M 25/10184* (2013.11); *A61M 2025/0002* (2013.01);
(Continued)

(58) Field of Classification Search
CPC ..... A61B 5/036; A61B 5/6853; A61B 5/4519; A61B 5/6812; A61B 2562/0247; A61M 25/10184; A61M 25/01; A61M 2025/0002
See application file for complete search history.

(56) References Cited

U.S. PATENT DOCUMENTS 3,721,229 A    3/1973    Panzer
4,192,319 A    3/1980    Hargens et al.
(Continued)

FOREIGN PATENT DOCUMENTS

CA    2961757    3/2016
CN    205649494    10/2016
(Continued)

OTHER PUBLICATIONS

International search report and written opinion for international application PCT/US2018/028687 dated Sep. 28, 2018.
(Continued)

*Primary Examiner* — Sean P Dougherty
(74) *Attorney, Agent, or Firm* — Neil D. Gershon

(57) ABSTRACT

A multi-lumen catheter for monitoring intramuscular pressure having an elongated body configured and dimensioned for insertion into a compartment of a patient. The catheter has a pressure sensor to determine if excessive pressure is being applied. A sensor is in communication with the lumen to continuously measure pressure to provide continuous readings of intramuscular pressure.

20 Claims, 16 Drawing Sheets

Related U.S. Application Data

(60) Provisional application No. 62/622,871, filed on Jan. 27, 2018, provisional application No. 62/514,793, filed on Jun. 3, 2017, provisional application No. 62/544,680, filed on Aug. 11, 2017, provisional application No. 62/590,513, filed on Nov. 24, 2017.

(51) Int. Cl.
*A61B 5/1455* (2006.01)
*A61M 25/00* (2006.01)
*A61M 25/10* (2013.01)

(52) U.S. Cl.
CPC ............... *A61M 2025/0003* (2013.01); *A61M 2025/1061* (2013.01)

(56) References Cited

U.S. PATENT DOCUMENTS

| | | | |
|---|---|---|---|
| 4,739,769 A | 4/1988 | Matthews et al. | |
| 4,873,986 A | 10/1989 | Wallace | |
| 4,901,731 A | 2/1990 | Millar | |
| 5,167,237 A | 12/1992 | Rabin et al. | |
| 5,447,497 A | 5/1995 | Sogard et al. | |
| 5,431,629 A * | 7/1995 | Lampropoulos et al. | 604/100 |
| 5,433,216 A | 7/1995 | Sugrue et al. | |
| 5,551,439 A | 9/1996 | Hickey | |
| 5,570,671 A | 11/1996 | Hickey | |
| 5,573,007 A | 11/1996 | Bobo, Sr. | |
| 5,697,375 A | 12/1997 | Hickey | |
| 5,707,358 A | 1/1998 | Wright | |
| 5,951,497 A | 9/1999 | Wallace et al. | |
| 5,980,485 A | 11/1999 | Grantz et al. | |
| 5,984,879 A | 11/1999 | Wallace et al. | |
| 6,021,781 A | 2/2000 | Thompson et al. | |
| 6,183,421 B1 | 2/2001 | Bobo | |
| 6,231,524 B1 | 5/2001 | Wallace et al. | |
| 6,434,418 B1 | 8/2002 | Neal et al. | |
| 6,447,462 B1 | 8/2002 | Wallace et al. | |
| 6,450,971 B1 | 9/2002 | Andrus et al. | |
| 6,461,332 B1 | 10/2002 | Mosel et al. | |
| 6,648,879 B2 | 11/2003 | Joye et al. | |
| 6,673,022 B1 | 1/2004 | Bobo et al. | |
| 6,723,053 B2 | 4/2004 | Ackerman et al. | |
| 6,827,710 B1 | 12/2004 | Mooney et al. | |
| 6,890,307 B2 | 5/2005 | Kokate et al. | |
| 7,081,096 B2 | 7/2006 | Brister et al. | |
| 7,347,822 B2 | 3/2008 | Brockway et al. | |
| 7,381,190 B2 | 6/2008 | Sugrue et al. | |
| 7,654,967 B2 | 2/2010 | Bobo, Sr. | |
| 7,722,544 B2 | 5/2010 | Williams et al. | |
| 7,828,753 B2 | 11/2010 | Euliano, II et al. | |
| 7,959,579 B2 | 6/2011 | Dijkman | |
| 7,976,475 B2 | 7/2011 | Dijkman | |
| 8,007,444 B2 | 8/2011 | Kokate et al. | |
| 8,192,368 B2 | 6/2012 | Woodruff et al. | |
| 8,235,426 B2 | 8/2012 | Pisula, Jr. et al. | |
| 8,337,411 B2 | 12/2012 | Nishtala et al. | |
| 8,360,988 B2 | 1/2013 | Bobo, Sr. et al. | |
| 8,403,884 B2 | 3/2013 | Nishtala | |
| 8,491,503 B2 | 7/2013 | Zaiken et al. | |
| 8,535,237 B2 | 9/2013 | Nishtala | |
| 8,596,688 B2 | 12/2013 | Pisula, Jr. et al. | |
| 8,626,316 B2 | 1/2014 | Mohl | |
| 8,636,724 B2 | 1/2014 | Wiita et al. | |
| 8,636,728 B2 | 1/2014 | Watson | |
| 8,646,325 B2 | 2/2014 | Hoem et al. | |
| 8,708,927 B2 | 4/2014 | Dijkman | |
| 8,876,729 B2 | 11/2014 | Bobo, Sr. et al. | |
| 9,046,205 B2 | 6/2015 | Whitaker et al. | |
| 9,055,949 B2 * | 6/2015 | Belfort | A61B 17/12099 |
| 9,101,314 B2 | 8/2015 | Shi | |
| 9,107,695 B2 | 8/2015 | Horton et al. | |
| 9,108,000 B2 * | 8/2015 | Kassab | A61B 5/02152 604/99.04 |
| 9,126,008 B2 | 9/2015 | Kim | |
| 9,167,973 B2 | 10/2015 | Steiner et al. | |
| 9,393,353 B2 | 7/2016 | Alam et al. | |
| 9,439,600 B2 | 9/2016 | Mohl | |
| 9,440,043 B2 | 9/2016 | Arora et al. | |
| 9,510,766 B2 | 12/2016 | Weed et al. | |
| 9,511,209 B2 | 12/2016 | Drasler et al. | |
| 9,534,721 B2 | 1/2017 | Lombardi, III | |
| 9,597,140 B2 | 3/2017 | Mihalik | |
| 9,622,670 B2 | 4/2017 | Burnett et al. | |
| 9,623,201 B2 | 4/2017 | Gregory et al. | |
| 9,655,555 B2 | 5/2017 | Burnett et al. | |
| 9,662,058 B2 | 5/2017 | Burnett et al. | |
| 9,662,670 B2 | 5/2017 | Veis et al. | |
| 9,695,966 B2 | 7/2017 | Lombardi, III et al. | |
| 9,713,494 B2 | 7/2017 | Nabutovsky et al. | |
| 9,717,472 B2 | 8/2017 | Ahmed et al. | |
| 9,724,232 B2 * | 8/2017 | Kassab et al. | A61F 7/123 |
| 9,734,706 B2 | 8/2017 | Moon et al. | |
| 9,757,545 B2 | 9/2017 | Kassab | |
| 9,782,115 B2 | 10/2017 | Shi | |
| 9,782,145 B2 | 10/2017 | Hart et al. | |
| 9,848,790 B2 | 12/2017 | Pintel | |
| 9,877,660 B2 | 1/2018 | O'Connell et al. | |
| 9,895,103 B2 | 2/2018 | Hyde et al. | |
| 9,913,585 B2 | 3/2018 | McCaffrey et al. | |
| 9,931,044 B2 | 4/2018 | Burnett et al. | |
| 9,931,122 B2 | 4/2018 | Burnett et al. | |
| 9,943,352 B2 | 4/2018 | Mihalik | |
| 10,004,551 B2 | 6/2018 | Burnett | |
| 10,194,813 B2 | 2/2019 | Bharucha et al. | |
| 10,206,575 B2 | 2/2019 | Al-Mayah | |
| 10,238,307 B2 | 3/2019 | Schlumpf et al. | |
| 10,314,488 B2 | 6/2019 | Satnuclsson et al. | |
| 10,368,872 B2 | 8/2019 | Franklin et al. | |
| 10,376,679 B2 | 8/2019 | Cox et al. | |
| 10,391,275 B2 | 8/2019 | Burnett et al. | |
| 10,433,741 B2 | 10/2019 | Stimpson | |
| 10,478,113 B2 | 11/2019 | Damaser et al. | |
| 10,485,483 B1 | 11/2019 | Brody | |
| 10,517,538 B2 | 12/2019 | Burnett et al. | |
| 10,531,834 B1 | 1/2020 | Smith et al. | |
| 10,532,193 B2 | 1/2020 | Fischer, Jr. et al. | |
| 10,537,274 B2 | 1/2020 | Damaser et al. | |
| 10,537,308 B2 | 1/2020 | Zhadkevich | |
| 10,542,924 B2 | 1/2020 | Imran et al. | |
| 10,568,686 B2 | 2/2020 | Lee | |
| 10,617,313 B2 | 4/2020 | Smith | |
| 10,631,788 B2 | 4/2020 | Brody | |
| 10,743,780 B2 | 8/2020 | Hoem et al. | |
| 10,750,999 B2 | 8/2020 | Parks et al. | |
| 10,758,135 B2 | 9/2020 | Burnett et al. | |
| 10,772,998 B2 | 9/2020 | Luxon | |
| 10,786,651 B2 | 9/2020 | Edminster et al. | |
| 2002/0143294 A1 * | 10/2002 | Duchon et al. | 604/131 |
| 2002/0183628 A1 | 12/2002 | Reich et al. | |
| 2003/0060800 A1 | 3/2003 | Ryan | |
| 2003/0114835 A1 | 6/2003 | Noda | |
| 2003/0181856 A1 * | 9/2003 | Goldman | 604/103.01 |
| 2004/0077976 A1 | 4/2004 | Wilson | |
| 2004/0127813 A1 | 7/2004 | Schwamm | |
| 2004/0171942 A1 | 9/2004 | Ackerman et al. | |
| 2005/0055043 A1 | 3/2005 | Foltz | |
| 2005/0065408 A1 | 3/2005 | Benderev | |
| 2005/0187430 A1 | 8/2005 | Aundal et al. | |
| 2005/0215989 A1 * | 9/2005 | Abboud | A61M 25/1018 606/21 |
| 2005/0240211 A1 | 10/2005 | Sporri | |
| 2005/0283092 A1 | 12/2005 | Gedebov | |
| 2006/0085022 A1 * | 4/2006 | Hayes | A61L 29/085 606/192 |
| 2006/0085024 A1 * | 4/2006 | Pepper | A61L 29/085 606/192 |
| 2007/0083126 A1 | 4/2007 | Marko et al. | |
| 2007/0197963 A1 * | 8/2007 | Griffiths etal. | 604/97.01 |
| 2007/0282219 A1 | 12/2007 | Holte | |
| 2008/0027358 A1 | 1/2008 | Gregersen et al. | |
| 2008/0077043 A1 | 3/2008 | Malbrain et al. | |
| 2008/0103408 A1 | 5/2008 | Denton et al. | |

(56) References Cited

U.S. PATENT DOCUMENTS

| | | |
|---|---|---|
| 2008/0146990 A1 | 6/2008 | Jenson et al. |
| 2009/0221993 A1 | 9/2009 | Sohi et al. |
| 2010/0056952 A1 | 3/2010 | Liu |
| 2010/0094204 A1 | 4/2010 | Nishtala |
| 2010/0094328 A1 | 4/2010 | O'dea et al. |
| 2010/0113939 A1 | 5/2010 | Mashimo et al. |
| 2010/0249663 A1 | 9/2010 | Nishtala |
| 2012/0041334 A1 | 2/2012 | Goedje et al. |
| 2012/0179063 A1 | 7/2012 | Bharucha et al. |
| 2012/0316460 A1 | 12/2012 | Stout |
| 2012/0316461 A1 | 12/2012 | Liu |
| 2013/0030262 A1 | 1/2013 | Burnett et al. |
| 2013/0046217 A1* | 2/2013 | Mooney ............... A61F 13/04 602/5 |
| 2013/0066166 A1 | 3/2013 | Burnett et al. |
| 2013/0079662 A1 | 3/2013 | Damaser et al. |
| 2014/0012305 A1 | 1/2014 | Horton et al. |
| 2014/0107550 A1* | 4/2014 | Paulson ............. A61F 5/05833 602/13 |
| 2014/0107573 A1 | 4/2014 | Wiita et al. |
| 2014/0155745 A1 | 6/2014 | Duncan |
| 2014/0200482 A1 | 7/2014 | Shi |
| 2015/0042406 A1 | 2/2015 | Kovac et al. |
| 2015/0133799 A1 | 5/2015 | O'Connell et al. |
| 2015/0327836 A1 | 11/2015 | Stone et al. |
| 2015/0342512 A1 | 12/2015 | Shi |
| 2015/0366498 A1 | 12/2015 | Choi et al. |
| 2016/0029912 A1 | 2/2016 | Stimpson |
| 2016/0066831 A1 | 3/2016 | Hyde et al. |
| 2016/0074581 A1 | 3/2016 | Gerrans |
| 2016/0106323 A1 | 4/2016 | Ou et al. |
| 2016/0183819 A1 | 6/2016 | Burnett et al. |
| 2016/0331294 A1 | 11/2016 | Imran et al. |
| 2016/0331451 A1 | 11/2016 | Nabutovsky et al. |
| 2016/0354028 A1 | 12/2016 | Damaser et al. |
| 2016/0374576 A1 | 12/2016 | Ziaie et al. |
| 2017/0055874 A1 | 3/2017 | Papirov et al. |
| 2017/0071566 A1 | 3/2017 | Hart et al. |
| 2017/0100561 A1 | 4/2017 | Burnett |
| 2017/0128012 A1 | 5/2017 | Parks et al. |
| 2017/0136209 A1 | 5/2017 | Burnett et al. |
| 2017/0156610 A1 | 6/2017 | Quackenbush et al. |
| 2017/0156611 A1 | 6/2017 | Burnett et al. |
| 2017/0160175 A1 | 6/2017 | Al-Mayah |
| 2017/0209048 A1 | 7/2017 | Wiita |
| 2017/0258345 A1 | 9/2017 | Smith |
| 2017/0259035 A1 | 9/2017 | Smith et al. |
| 2017/0332955 A1 | 11/2017 | Burnett et al. |
| 2018/0049658 A1 | 2/2018 | Smith |
| 2018/0177458 A1 | 6/2018 | Burnett et al. |
| 2018/0184929 A1 | 7/2018 | Burnett et al. |
| 2018/0311469 A1 | 11/2018 | Wiita |
| 2018/0344183 A1 | 12/2018 | McKinney et al. |
| 2018/0344234 A1 | 12/2018 | McKinney et al. |
| 2018/0344250 A1 | 12/2018 | McKinney et al. |
| 2019/0282109 A1 | 9/2019 | Schlumpf et al. |
| 2019/0321588 A1 | 10/2019 | Burnett et al. |
| 2019/0343445 A1 | 11/2019 | Burnett et al. |
| 2020/0029906 A1 | 1/2020 | Smith et al. |
| 2020/0046237 A1 | 2/2020 | Stimpson |
| 2020/0085378 A1 | 3/2020 | Burnett et al. |
| 2020/0237242 A1 | 7/2020 | Kaluzny et al. |

FOREIGN PATENT DOCUMENTS

| | | |
|---|---|---|
| EP | 0097454 | 1/1984 |
| WO | WO 1995/012351 | 5/1995 |
| WO | WO 2005/013834 | 2/2005 |
| WO | WO 2006/060248 | 6/2006 |
| WO | WO 2011/053500 | 5/2011 |
| WO | WO 2012/006624 | 1/2012 |
| WO | WO 2012/006625 | 1/2012 |
| WO | WO 2014/160300 | 10/2014 |
| WO | WO 2014/210453 | 12/2014 |
| WO | WO 2015/191125 | 12/2015 |
| WO | WO 2016/049654 | 3/2016 |
| WO | WO 2016/204631 | 12/2016 |
| WO | WO 2017/156451 | 9/2017 |
| WO | WO 2018/136306 | 7/2018 |

OTHER PUBLICATIONS

International search report and written opinion for international application PCT/US2018/028693 dated Sep. 28, 2018.

International search report for international application PCT/US2018/034781 dated Sep. 5, 2018.

International search report for international application PCT/US2018/032467 dated Sep. 5, 2018.

Extended European Search Report dated Mar. 2, 2020 for European Application No. EP 19210264.8.

\* cited by examiner

CATHETER FOR MONITORING PRESSURE FOR MUSCLE COMPARTMENT SYNDROME

This application claims priority from provisional application Ser. No. 62/622,871, filed Jan. 27, 2018, and is a continuation in part of application Ser. No. 15/949,005, filed Apr. 9, 2018, which claims the benefit of provisional application Ser. No. 62/514,793, filed Jun. 3, 2017, provisional application Ser. No. 62/544,680, filed Aug. 11, 2017, provisional application Ser. No. 62/590,513, filed Nov. 24, 2017 and provisional application Ser. No. 62/622,871, filed Jan. 27, 2018. The entire contents of each of these applications are incorporated herein by reference.

BACKGROUND OF THE INVENTION

1. Field of the Invention

This application relates to a device and method for monitoring intramuscular pressure in patients having muscle compartment syndrome.

2. Background

Muscle compartment syndrome (MCS) is a painful and potentially deadly condition that occurs when intramuscular pressure, i.e., pressure within a muscle "compartment," builds to dangerous levels. The compartments are well defined spaces made up of bones and fascial envelopes (connective tissues). For example the anterior compartment of the leg, where the syndrome often strikes, is delineated by the tibia bone on the inside, the fibula bone to the rear, and the crural fascia that surrounds the muscles. Since the tibia and fibula are both bones, they don't offer any flexibility. The result is there is no "give" or room for muscle expansion on either side of the anterior compartment. This pressure within the muscle compartment can decrease blood flow, preventing nourishment and oxygen from reaching nerve and muscle cells. MCS occurs because muscles, nerves, and blood vessels are covered and held in place by a tough membrane called a fascia that does not stretch or expand easily. Because the fascia does not stretch, swelling or bleeding within the muscle compartment can cause increased pressure on the capillaries, nerves and muscles, disrupting blood flow. Without a steady supply of oxygen and nutrients, muscle and nerve cells can be damaged and necrosis occurs releasing toxins that can cause a deadly process called disseminating intravascular coagulopathy eating up clotting factors leading to severe bleeding.

MCS most often occurs in the anterior (front) compartment of the lower leg (calf) or thigh, but can also occur in the other compartments in the leg, e.g., lateral and posterior, as well as in the arms, hands, feet and buttocks. MCS can be acute or chronic.

Acute MCS is a medical emergency, usually caused by a severe injury. Conditions that may bring on acute MCS include for example bone fracture, or bad contusions and bruising, e.g., when a football player is hit in the leg with another player's helmet. These acute injuries followed by reestablished blood flow after circulation has been blocked, e.g., after a surgeon repairs a damaged bone and blood vessels that has been blocked for several hours, crash/crushing injuries, anabolic steroid use, constricting bandages, etc. In acute MCS, unless the pressure is relieved quickly, permanent disability and tissue death may result. The classic sign of acute MCS is pain, especially when the muscle within the compartment is stretched. There may also be tingling or burning sensations (paresthesisas) in the skin, and the muscle may feel tight or full. Numbness and paralysis are late signs of compartment syndrome, usually indicating permanent tissue injury. Acute MCS is a surgical emergency treated by cutting open the skin and fascia covering the affected compartment (fasciotomy). This is invasive surgery and involves making a long incision, such as from the ankle to the knee, in the fascia of both compartments in the lower leg—the anterior and the lateral—to release the pressure. There is no effective nonsurgical treatment.

Chronic compartment syndrome, also known as exercise-induced or exertional compartment syndrome, is most often caused by athletic exertion, and is usually not a medical emergency. Chronic MCS causes pain or cramping during exercise that typically subsides when activity stops. Symptoms may also include, numbness, difficulty moving the impacted limb and visible muscle bulging. Chronic MCS is typically treated by avoiding the activity that caused the condition, or with physical therapy, orthotic shoe inserts and/or anti-inflammatory medicines. Fasciotomy is required in some instances. These are common in professional athletes and weekend warrior athletes.

It is estimated that the annual number of MCS pressure measurements is fewer than 15,000 and 30,000 in the US and worldwide, respectively, due to the absence of a simple continuous monitoring both static and during exercise, as well as a cost-effective measurement device. It is notable however, that the following patients are most likely to require fasciotomy and would therefore benefit from timely, accurate measurement of muscle compartment pressure: athletes who have sustained serious impact-injuries, people who spend long periods of time on their feet, people with severe burns, persons who are overweight, compartment infectious/sepsis and snakebite victims.

There are several other injuries/conditions which would benefit from pressure measurement. For example, there are many orthopedic injuries requiring casting. An orthopedic cast, also known as a plaster or surgical cast, is a plaster or fiberglass shell that encases a limb or large portions of the body to stabilize and hold anatomical structures in place until healing is confirmed. No existing devices can monitor pressure after casting, therefore, it would be beneficial to provide a pressure measuring device which can be set in place before casting, and reside within the cast for an extended period of time (e.g., up to one week or even several weeks) to monitor for pressure increases that present a risk of damage or death to muscle and nerves.

Such pressure measurement could also be useful in military applications, i.e., to monitor MCS in combat wounds to determine whether fasciotomy is indicated.

MCS measurement could also be beneficial for treatment of Carpel Tunnel Syndrome. Carpal tunnel syndrome (CTS) occurs when the tissue surrounding the flexor tendons in the wrist swell and put pressure on the median nerve, causing numbness, tingling, or burning sensations and weakness in the thumb and forefingers. These symptoms can be caused by other neurological diseases or occur in other areas of the body, C-Spine for example. At present the operation is done with the hope the function returns. By measuring the pressure before the release, the success of the surgery can be predicted and unnecessary surgeries prevented. It will also help doctors medical-legally documenting the need for the release surgery. In the U.S., CTS affects over three million people annually, with approximately 260,000 carpal tunnel release operations performed each year.

Another potential application for a simple accurate pressure measurement device is Occipital Neuralgia/Migraine. Occipital neuralgia (ON) is characterized by piercing, stabbing, sharp pain in the occipital nerves, lasting a few seconds to minutes. It is a relatively rare disorder affecting 3.2 people/100,000 annually. The cause of ON is unknown, but compression of the occipital nerves by arteries or tumors is one of several hypotheses. Ongoing research has tied occipital nerve compression with migraine headaches and release can eliminate some forms of migraines which effects millions at patients each year.

Therefore, the need exists for a device for simple and accurate intramuscular pressure monitoring/measurement for individuals suffering from muscle compartment syndrome as well as other conditions.

SUMMARY

The present invention overcomes the disadvantages and deficiencies of the prior art. This is accomplished by a simple, accurate pressure monitoring system which can determine intramuscular pressure for muscle compartment syndrome and other conditions. The catheters of the present invention utilize in some embodiments a micro-tip sensor, and in other embodiments, a gas, e.g., air, charged chamber, to measure intramuscular pressure and in some embodiments enable pressure to be measured continuously if desired. Various types of sensors and different locations of the sensors are utilized with the several embodiments of the catheters of the present invention, each discussed in detail herein.

Some embodiments of the catheter enable implantation within the body or within an orthopedic cast for an extended period of time. This is discussed in more detail below, In some embodiments, the catheters are inserted through an introducer sheath, and then the introducer sheath is removed. These steps of insertion are discussed below.

In accordance with one aspect of the present invention, a multi-lumen catheter for monitoring intramuscular pressure is provided comprising an elongated body configured and dimensioned for insertion into a compartment of a patient. The catheter has a lumen and a balloon at a distal portion, the lumen communicating with the balloon. The balloon contains a gas to form along with the lumen a gas containing chamber to monitor intramuscular pressure to thereby determine if excessive pressure is being applied. A sensor is in communication with the lumen to measure pressure about a circumferential area of the balloon to provide readings of intramuscular pressure. In some embodiments, the pressure can be measured continuously to provide continuous readings.

In accordance with another aspect of the present invention, a system for monitoring intramuscular pressure is provided. The system includes an introducer sheath and a catheter dimensioned and configured for insertion through the introducer sheath to access a muscle compartment of the patient. The catheter includes an elongated body having a first lumen and a pressure sensor. The pressure sensor is positioned within a distal region of the lumen, the sensor monitoring pressure within the muscle compartment to thereby assess if pressure beyond a predetermined pressure is being applied due to excess fluid in a muscle of a patient.

In accordance with another aspect of the present invention, a method for monitoring intramuscular pressure is provided comprising the steps of:

inserting an introducer sheath into a muscle compartment of a patient;

inserting through the introducer sheath a catheter having a lumen and a sensor, a distal portion of the catheter extending into the muscle compartment;

removing the introducer sheath leaving the catheter within the muscle compartment;

obtaining a first pressure reading of intramuscular pressure due to excess fluid in a muscle causing increased pressure; and transmitting the first pressure reading to an external monitor in communication with the catheter to indicate pressure, the indicated pressure informing if intramuscular pressure exceeds a threshold pressure.

In accordance with another aspect of the present invention, a method for measuring intramuscular pressure within a carpal tunnel of a patient to determine if surgery is warranted is provided, the method comprising the steps of:

inserting a catheter having a lumen and a sensor into the carpal tunnel;

obtaining a first pressure reading of intramuscular pressure in the carpal tunnel due to excess fluid in a muscle causing increased pressure in the surgically opened carpal tunnel; and transmitting the first pressure reading to an external monitor in communication with the catheter to indicate pressure, the indicated pressure informing if intramuscular pressure exceeds a threshold pressure.

In accordance with another aspect of the present invention, a method for measuring intramuscular pressure within an orthopedic cast on a body is provided comprising the steps of:

positioning a device having a lumen and a pressure sensor within an orthopedic cast so a distal portion of the device containing the pressure sensor is retained within the cast and a proximal portion is exposed from the cast;

connecting the device to an external pressure monitor;

obtaining a first pressure reading of intramuscular pressure within the cast;

transmitting the first pressure reading to the external monitor in communication with the device to indicate pressure, the indicated pressure informing if intramuscular pressure exceeds a threshold pressure; and leaving the device within the cast for an extended period of time to obtain multiple pressure readings over the extended period of time.

In some embodiments, pulse-oximeter readings can be provided as well as pressure readings.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIGS. 8A, 8B, 8C, 8D and 8E show one embodiment of a method of insertion of the catheter of the present invention, wherein FIG. 8A is a side view illustrating the introducer sheath with the insertion needle positioned therein;

FIG. 8B is a side view of the insertion needle prior to introduction into the sheath;

FIG. 8C is a side view similar to FIG. 8A showing the introducer sheath and insertion needle positioned within tissue;

FIG. 8D is a side view of the catheter of FIG. 2 prior to insertion into the introducer sheath; and FIG. 8E illustrates the catheter remaining in the tissue after removal of the introducer sheath to access and provide pressure readings and further shows schematically the catheter electrically connected to a pressure monitor;

DETAILED DESCRIPTION OF PREFERRED EMBODIMENTS

Figure 1A:
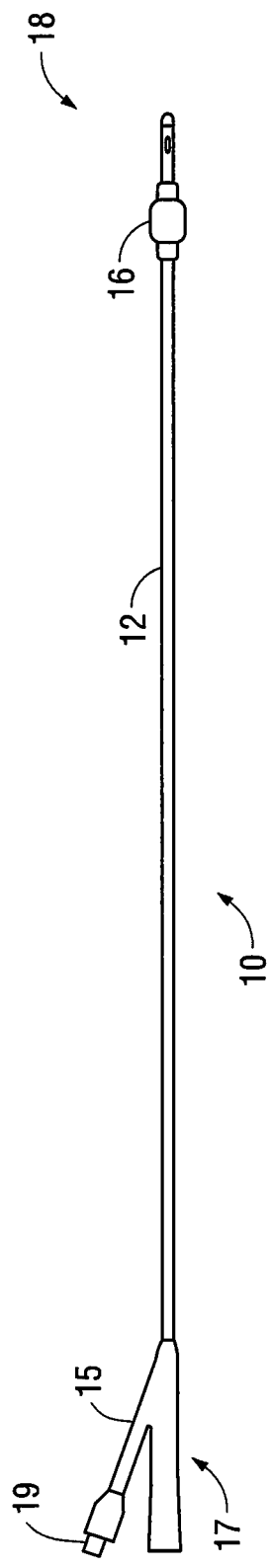
FIG. 1A is a side view of a first embodiment of the catheter of the present invention having a pressure sensing balloon and a side port for balloon inflation, the balloon shown in the inflated (expanded) condition.

The catheters of the present invention are designed to monitor/measure intramuscular pressure, preferably continuously, in conditions such as muscle compartment syndrome (MCS). In MCS, intramuscular pressure builds to dangerous levels, and if not relieved, can decrease blood flow, preventing nourishment and oxygen from reaching nerve and muscle cells. MCS occurs because muscles, nerves, and blood vessels are covered and held in place by a tough membrane called a fascia that does not stretch or expand easily. Because the fascia does not stretch, swelling or bleeding within the muscle compartment can cause increased pressure on the capillaries, nerves and muscles, disrupting blood flow. Without a steady supply of oxygen and nutrients, muscle and nerve cells can be damaged. MCS, as discussed above, most often occurs in the anterior (front) compartment of the lower leg (calf) or thigh, but can also occur in the other compartments in the leg, as well as in the arms, hands, feet and buttocks. MCS can be acute or chronic, with acute requiring quick release of pressure to prevent permanent disability and tissue death. The catheters of the present invention provide a simple portable device that can measure intramuscular pressure and is connectable to a pressure monitor to provide pressure readouts so steps can be taken if the pressure exceeds a predetermined threshold. The catheter can be connected via a cable or wires, or alternatively, through a wireless connection, to a hand held monitor and/or a Unit Central Station. Also, a multitude of sensors can be provided and monitored simultaneously.

The catheters of the present invention can also be used for carpal tunnel syndrome, occipital neuralgia (ON) as well as military uses as will be described in more detail below. Determination of muscle conditions can be utilized by medical personnel to assess whether certain surgeries should be undertaken.

An alarm system can also be provided with the catheter to provide an alert if pressure exceeds a predetermined threshold.

Thus, the present invention provides a device/system and method to protect and reduce the risk of harm by excess intramuscular pressure. In preferred embodiments, constant (continuous) monitoring of pressure is provided so critical time periods are not missed.

The catheters of the present invention utilize in some embodiments a gas (e.g., air) charged chamber to measure intramuscular pressure across a large surface area. In other embodiments, the catheters of the present invention utilize a microtip pressure sensor at a distal end of the catheter to measure intramuscular pressure. In either case, the sensor provides the physician with real-time information on increasing intramuscular pressure so appropriate steps can be taken. The pressure measurement can also assist physicians in determining whether surgical procedures are indicated.

By determining the muscle pressure conditions, the medical personnel can determine if steps need to be taken to relieve the pressure such as by cutting open the skin and fascia covering the effective compartment (fasciotomy).

The catheters of the present invention can be utilized in an "unsheathed version" or a "sheathed version." In the unsheathed version, the catheter is inserted directly into the body such as into a surgically-opened muscle/fascial "tunnel" to take an instantaneous pressure reading. This variant can include "tunnel syndromes" such as a Carpel Tunnel Syndrome (CTS), to assess whether elevated pressure is the cause of the patient's pain. CTS surgery is contraindicated if pressure is not elevated. In the sheathed version, the catheter is inserted through an introducer sheath which is inserted into the muscle via an intravenous needle. The intravenous needle is pulled out leaving the sheath inserted, and the catheter is subsequently inserted, leaving the catheter in the introducer sheath. The sheath can then be removed leaving the catheter in position so the sensor is within the muscle compartment. An ultrasound guided needle placement into the carpal-tunnel area can be utilized to allow placement of the pressure sensor in the space without an operation for proper diagnosis.

The catheter can be reused among the same patient's muscle compartments, but is preferably otherwise disposable.

Another use of the catheter of the present invention is with orthopedic casting. An orthopedic cast, also known as a plaster or surgical cast, is a plaster or fiberglass shell that encases a limb or large portions of the body to stabilize and hold anatomical structures in place until healing is confirmed. The catheters of the present invention in certain embodiments can be set in place before casting, and reside within the cast for an extended period of time (e.g., several weeks) to monitor for pressure increases that present a risk of damage or death to muscle and nerves. In some embodiments, a multitude of sensors can be left in and monitored before the cast goes on. In some embodiments, multiple catheters can be placed within the cast for measuring pressure in multiple muscles.

Referring now to the drawings and particular embodiments of the present invention wherein like reference numerals identify similar structural features of the devices disclosed herein, there is illustrated in FIG. 1A a catheter of a first embodiment of the present invention. The catheter (device) is designated generally by reference numeral 10 and is configured for insertion into and positioning within a muscle compartment of the patient for measuring intramuscular pressure. Such intramuscular pressure is a result of the muscles expelling fluid after injury or other conditions, and the fluid fills the spaces and exerts pressure on the compartment.

Turning now to details of the catheter 10, which is also referred to herein as the device 10, and with initial reference to FIG. 1A, the catheter 10 has an elongated shaft 12 having a lumen (channel) extending within the shaft 12 and communicating at its distal region 18 with balloon 16 to fluidly communicate with balloon 16 to inflate the balloon. Balloon 16 is utilized for monitoring pressure and is sometimes referred to herein as the "pressure balloon 16." A side port 15 is positioned at a proximal region 17 of the catheter 10 for communication with an infusion source for infusion of gas, e.g., air, through the lumen and into the balloon 16. The catheter 10 is shown in FIG. 1A with balloon 16 in the inflated (expanded) condition (position) for positioning within the compartment. It is inserted into the compartment in the deflated (collapsed) condition (position).

Figure 1B:
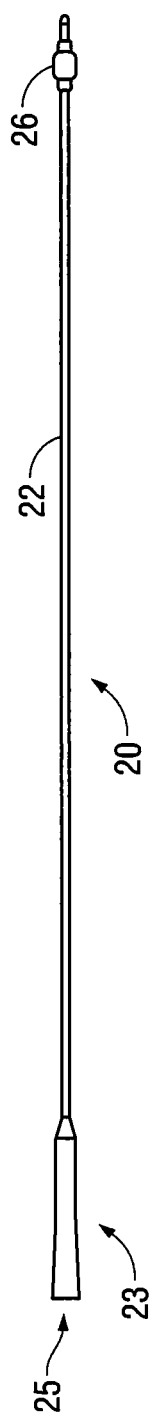
FIG. 1B is a side view of an alternate embodiment of the catheter of the present invention having a pressure sensing balloon.
Figure 1C:
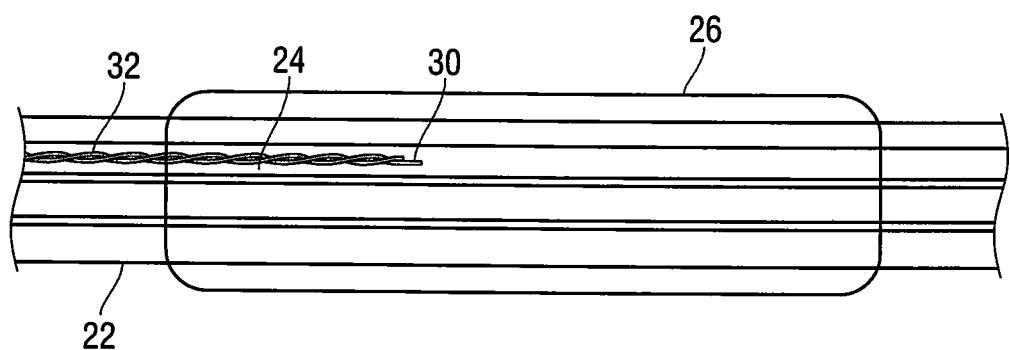
FIG. 1C is a close up view of the catheter of FIG. 1A, the balloon shown in the deflated condition.
Figure 7:
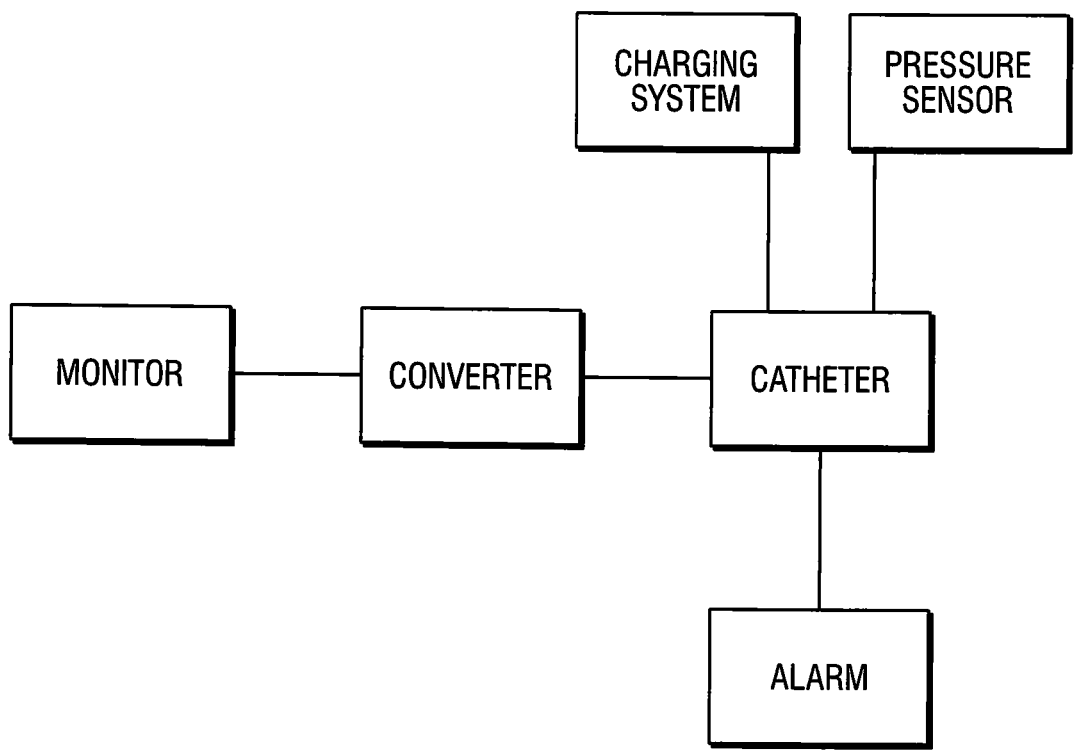
FIG. 7 is a schematic view of one embodiment of the system of the present invention utilizing the catheter of FIG. 1A with an alarm system.

In an alternate embodiment of FIG. 1B, a side port is not provided and gas, e.g., air, is injected through the opening 25 at proximal end 23 of catheter 20 and passes through the lumen 24 in shaft 22 into pressure balloon 26. A sensor 30 (FIG. 1C) is positioned within the lumen 24 of shaft 12 communicating with opening 25 (or in the lumen in shaft 12 communicating with opening 19 in side port 15 of FIG. 1A). The sensor 30 is positioned adjacent the balloon 16 to measure intramuscular pressure. Wires 32 extend from the sensor 30 through the lumen 24. The wire(s) 32 are shown extending through lumen 24 to communicate external of the catheter, the sensor 30 and wire(s) 32 being of sufficiently small size so as not to interfere with gas (e.g., air) flow though lumen 24. The sensor 30 is part of a transducer for converting the variation in pressure to an electrical signal for transmission to an external monitor. The transducer can be wired directly to the monitor or alternatively wired to a converter external of the catheter for converting the signal received by the transducer and transmitting a signal to the monitor, e.g., a handheld monitor, to display the pressure readings. This is shown schematically in FIG. 7. The readings can be displayed in quantitative form, graphical form or other displays to provide an indicator to the clinician of the intramuscular pressure. Alternatively, the sensor/transducer can be connected to the monitor via a Bluetooth wireless connection. It can be connected to a hand held monitor or to a central unit command.

The wire(s) 32 can extend through lumen 24, exiting through or terminating at proximal opening 25, or in the embodiment of FIG. 1A, extending through the lumen in shaft 12 of catheter 10, exiting through or terminating at opening 19 at side port 15, for connection to a converter or monitor or alternatively can be inserted through the lumen, piercing the wall of the lumen to enter the lumen distal of the side port.

An indicator or alarm system can also be provided wherein the system includes a comparator for comparing the measured pressure to a threshold (predetermined) value, and if such threshold is exceeded, an indicator, e.g., an alarm, is triggered to indicate to the clinician the excessive pressure. An alarm system can alternatively or in addition be activated if a change in pressure measurement exceeds a specified rate over a specified period of time. This would alert the staff to an imminent risk of pressure exceeding a certain threshold or predetermined value (pressure). The indicator or alarm can be on (part of) the catheter or alternatively on an external device such as the monitor. The alarm can also be connected via wireless connection to a phone or remote device to alert the appropriate personnel. Such indicator or alarm system can be utilized with any of the embodiments disclosed herein. In embodiments wherein other parameters are measured, the alarm system described herein can be tied into measurement of these parameters.

The lumen 24 and space within balloon 26 together form a closed air (or other gas) chamber, i.e., the lumen 24 forming an air column. (A similar air (or other gas) chamber is formed in the lumen and space within balloon 16 in the embodiment of FIG. 1A). With the balloon 26 (or balloon 16) filled with air (or other gas), pressure on the external wall of the balloon 26 will force the balloon to deform inwardly, thereby compressing the air (or other gas) contained within the balloon space and within the lumen 24. The pressure sensor 30 is located in a distal portion of the lumen 24 at the region of the balloon 26 and thus is positioned at the distal end of the air column. Therefore, the pressure is sensed at the distal region as the sensor 30 detects change in pressure in lumen 24 due to balloon deformation. Placement of the sensor 30 at a distal location provides a pressure reading closer to the source which in some applications can increase the accuracy by reducing the risk of transmission issues by reducing the amount of interference which could occur due to water, air, clots, tissue, etc. if the transmission is down the gas, e.g., air, lumen (air column).

Additionally, the pressure measurement occurs about a circumferential area of the balloon 26 (or balloon 16) providing a pressure reading of a region greater than a point pressure sensor reading. Also, average pressure over an area of the wall can be computed. Thus, the area reading gleans information on pressure over more of the wall of the compartment. Stated another way, the balloon has a relatively large surface area with multiple reference points to contribute to average pressure readings of the surface around it.

The air column is charged by insertion of air through the proximal opening 25 (or through side port 15 of catheter 10) which communicates with lumen 24. The opening 25 (or side port 15) includes a valve to provide a seal to prevent escape of air from a proximal end. The balloon 26 (or 16) can be composed of impermeable material, or in alternative embodiments, a permeable or semi-permeable material with an impermeable coating. This seals the air column at the distal end to prevent escape of air through the distal end, i.e., through the wall of the balloon 26 (or 16). Thus, with the lumen sealed at the proximal and distal ends, a closed air (or other gas) system (air charged system) is provided.

In preferred embodiments, when the lumen is gas, e.g., air, charged, the balloon 26 (or 16) is not fully inflated. This improves the accuracy of the balloon transmitting pressure from external the balloon to the interior of the balloon and into the lumen, i.e., air column, by ensuring the balloon has sufficient compliancy to prevent the balloon from introducing artifact into the pressure reading which would diminish its accuracy. That is, in preferred embodiments, the pressure balloon 26 (or 16) is not fully inflated so it would receive less than the maximum volume. Thus, with a balloon of maximum X volume, the balloon would receive X-Y fluid, with Y representing the amount of desired extra space to achieve desired compliancy of the balloon while still enabling sufficient inflation of the balloon to achieve its pressure induced deformation function. Thus, the use herein of gas or air filled chamber or balloon or lumen filled with gas encompasses the balloon completely filled or partially filled. The term gas containing chamber is therefore also used herein.

Figure 2:
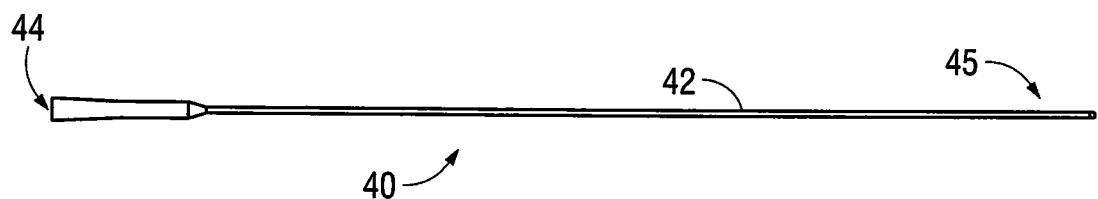
FIG. 2 is a side view of an alternate embodiment of the catheter of the present invention having a micro-tip sensor.

In the alternate embodiment of FIG. 2, instead of a pressure balloon, a microtip sensor is positioned within the lumen. More specifically, catheter 40 has a shaft 42 with a lumen terminating at a proximal opening 44. The sensor is positioned at a distal region 45 and wire(s) extend from the sensor through a lumen in the shaft 42, communicating at a proximal end with a cable for connection to a pressure monitor. That is, the microtip sensor measures pressure within the muscle compartment and transmits such measurements to an external monitor either through a wire or a wireless connection. Preferably, the sensor provides continuous readings, although intermittent readings are also contemplated as explained herein with regard to other embodiments. In an alternate embodiment, instead of the microtip sensor, a fiber optic sensor can be provided to provide intramuscular pressure measurements.

Note that although only one sensor is provided and shown in the Figures, it is also contemplated that multiple sensors can be provided in the catheter. Also, note that the sensor 30 is positioned in lumen 24 at a mid-portion of the balloon, i.e., just proximal where the opening in lumen 24 communicates with the interior of the balloon 26. It is also contemplated that the sensor can be placed at another portion within the lumen 24, e.g., a more proximal portion with respect to the lumen opening. Also, the lumen opening need not be at the mid portion of the balloon and can be at other regions of the balloon to communicate with the interior space. Note if multiple sensors are provided, they can be positioned at various locations within the lumen 24.

As shown, the sensor 30 and its transmission wires are located in the same lumen 24 used for inflation fluid, e.g. air, for balloon 26 (or 16) and for the gas (e.g., air) charged column. This minimizes the overall transverse cross-section (e.g., diameter) of the catheter 20 by minimizing the number of lumens since additional lumens require additional wall space of the catheter. However, it is also contemplated in alternate embodiments that the sensor is located in a dedicated lumen separate from the pressure balloon inflation lumen. This can be useful if a larger sensor or additional wires are utilized which would restrict the air (gas) lumen if provided therein. This is also useful if a specific sized lumen for the sensor and wires is desired to be different than the sized lumen for the air column. Thus, in this embodiment, the catheter would have two lumens: 1) a lumen for filling the pressure balloon; and 2) a lumen in which the sensor (similar to sensor 30) and its transmission wires (similar to wires 32) are contained. In the embodiment of FIG. 1A, two lumens can be provided wherein one lumen can be used for the wires connecting to a cable at a proximalmost end while the balloon is inflated via a separate lumen in fluid communication with the side port. Alternatively, one lumen can be used for both inflation and the wires and the other lumen can be used for fluid passage into the patient's body.

Turning now to the use of the catheter 20 (catheter 10 would be used in the same way), the system is charged by inflation of the balloon 26 (or 16), i.e., preferably partial inflation for the reasons discussed above, by insertion of air (or other gas) via a syringe or other inflation device through proximal opening 25 (or port 15) which is in fluid communication with lumen 24. As discussed above, the catheter 20 (and catheter 10) is a closed system with the balloon 26 (or 16) sealed so that air (or other gas) inserted through lumen 24 and into balloon 26 cannot escape through balloon 26. Thus, a closed chamber is formed comprising the internal space of the balloon 26 and the internal lumen 24 communicating with the internal space. With the balloon 26 inflated, pressure monitoring commences. When external pressure is applied to an outer surface of the balloon 26, caused by outward pressure against the wall of balloon 26 due to the pressure within the muscle compartment, the gas within the chamber is compressed. The sensor 30 at the distal end of lumen 24 can provide continuous pressure readings, converted to an electrical signal by the transducer within the distal end of lumen 24, and then electrically communicates through wire(s) 32 extending through lumen 24, exiting through the proximal opening 25 (or side port 15) and connected to an external monitor. This enables determination of the pressure inside the compartment to ensure it does not reach a level (a predetermined level or threshold) where it could damage the muscle and/or nerve cells or other tissue. Note the wire(s) can terminate at the proximal end in a plug in connector which can be connected directly to the monitor or alternatively plugged into a converter to convert the signals from the transducer in the embodiments wherein the converter is interposed between the wires and monitor (see e.g., the system of FIG. 7) to provide the aforedescribed graphic display. Although, the system is capable of continuous pressure monitoring, it can also be adapted if desired for periodic monitoring so the pressure readings can be taken at intervals or on demand by the clinician.

The balloon 26, like balloon 16, can be of sufficiently large size to provide a sufficient circumferential area for detection of pressure changes along several parts of the compartment wall, thereby providing an average pressure and enabling more accurate pressure readings. That is, the pressure balloon has a large circumferential area (and large volume) to provide multiple reference points for pressure readings and to provide an average pressure to enable more accurate readings. Thus, the pressure balloon provides for gross measurement. Other shapes and sizes of the pressure balloon can be provided as an alternative to the pressure balloon 26 illustrated in the drawings.

Note that the catheter 20 (and 10) can be inserted directly into the muscle compartment (an unsheathed version) or inserted through a sheath 60 as discussed below. Similarly, the catheter 40 with the microtip sensor can be inserted directly into the muscle compartment (an unsheathed version) or inserted through a sheath 60.

In the embodiments wherein an indicator is provided, if the measured pressure exceeds a threshold value, and/or a change in pressure measurement exceeds a specific rate over a specific time period, the indicator would alert the clinician, e.g., via a visual indication or an audible indication, that the threshold is exceeded. The indicator in some embodiments can include an audible or visual alarm (shown schematically in FIG. 7). In the embodiments having an indicator, the indicator can be provided on a proximal end of the catheter which extends out of the patient or the indicator can be part of an external component such as the monitor or a separate alarm system. A visual, audible, or other indicator can likewise be provided in any of the other embodiments disclosed herein to indicate if the measured pressure exceeds a predetermined value or pressure change exceeds a specific rate, and such indicator can include an alarm and can be part of the catheter or a separate component.

In an alternate embodiment, the catheter can include a pressure sensor within the balloon. That is, the pressure sensor is carried by the catheter and positioned within the balloon to measure pressure in response to deformation of the balloon in response to pressure exerted on an outer wall of the balloon due to intramuscular pressure. In alternate embodiments, the pressure transducer is positioned external of the catheter rather than in the gas lumen or balloon. That is, instead of the pressure transducer including the sensor being positioned within the distal end of the gas (e.g., air) lumen, the pressure sensor is positioned within a lumen at the distal end of the lumen and transmission wire(s) connect the sensor to the pressure transducer positioned outside of the patient at a proximal region of the catheter. The pressure transducer can be positioned in a side port of the catheter or in alternate embodiments, positioned outside the catheter. Alternatively, the pressure transducer and the pressure sensor can be positioned at a proximal end of the catheter or alternatively positioned external of the patient adjacent a proximal region of the catheter rather than in the gas lumen. That is, instead of the pressure sensor being positioned within and at the distal end of the gas lumen, the transducer and pressure sensor can be positioned in a side port. In yet other embodiments, the pressure sensor and/or pressure transducer can be positioned within the gas lumen at a proximal end of the gas lumen. In the foregoing systems, the system is charged by inflation of the balloon, i.e., preferably partially inflated for the reasons discussed above, by insertion of air (or other gas) via a syringe through the side port which is in fluid communication with the air lumen or through a proximal end of the air lumen. The catheters like the aforementioned catheters are closed systems with the balloon sealed so that air (or other gas) inserted through the lumen and into the balloon cannot escape through the balloon—a closed chamber is formed comprising the internal space of the balloon and the internal lumen communicating with the internal space of the balloon. Pressure applied against the balloon wall compresses the balloon and the air (or other gas) within the chamber of the balloon, compressing the air within the lumen creating an air charged column along the lumen, with the sensor at the proximal end of the catheter measuring pressure of the air column, preferably providing continuous pressure readings, converted to an electrical signal by the transducer, and then electrically communicating through wire(s) to an external monitor.

Note the wires of the sensor can terminate at the proximal end in a plug in connector which can be connected directly to the monitor or alternatively plugged into a converter to convert the signals from the transducer in the embodiments wherein the converter is interposed between the wires and monitor to provide the aforedescribed graphic display. Although, the system is capable of continuous pressure monitoring, it can also be adapted if desired for periodic monitoring so the pressure readings can be taken at intervals or on demand by the clinician.

FIGS. 3A-5 illustrate an alternate embodiment of the catheter of the present invention. The pressure balloon for detecting pressure is designated by reference numeral 92. The balloon 92 functions in the same manner as balloon 26 (and balloon 16) of FIG. 1B so further discussion is not warranted. That is, the discussion of the compliant balloon 26 of the embodiment of FIG. 1B (and balloon 16), i.e., compression of the outer wall of the balloon compresses the air (or other gas) within the air (or other gas) lumen, is fully applicable to catheter 90 of FIGS. 3A-5.

Figure 3A:
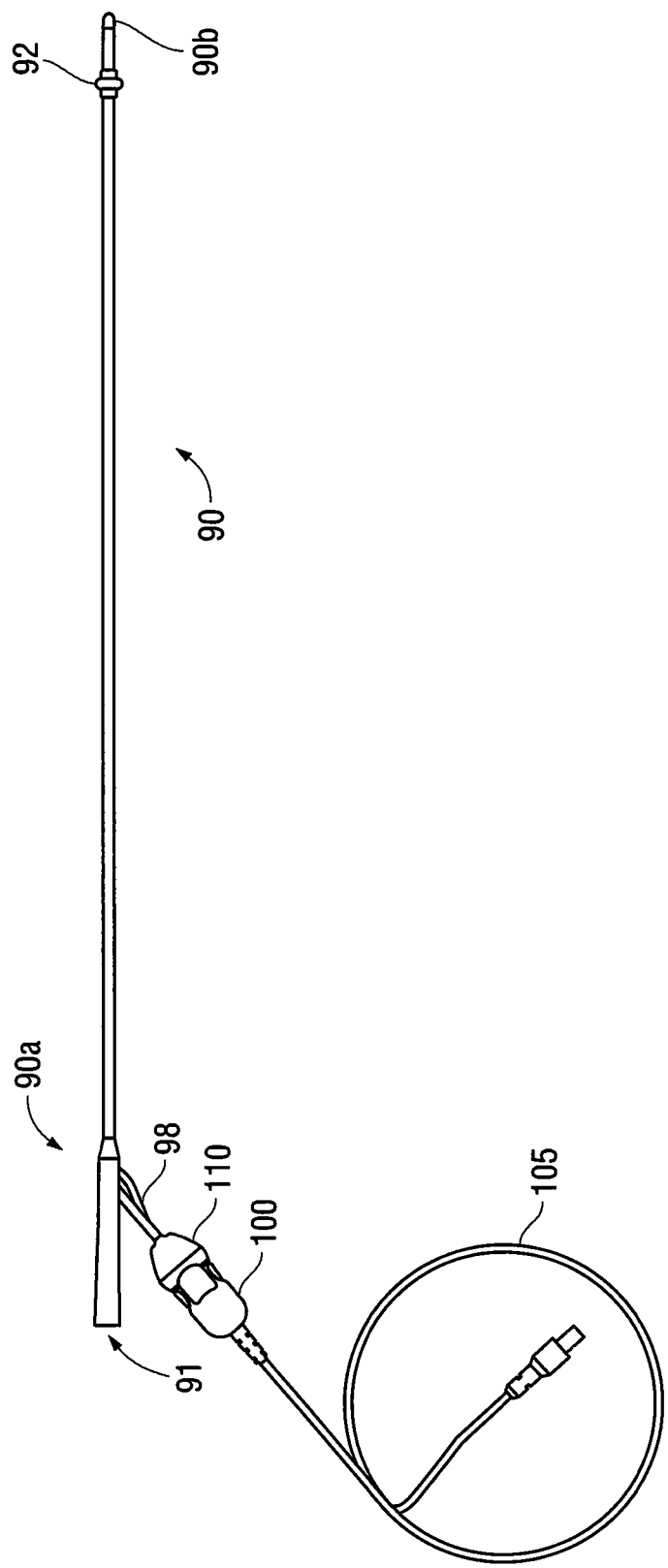
FIG. 3A is a side view of an alternate embodiment of the catheter of the present invention having a pressure sensing balloon.
Figure 3B:
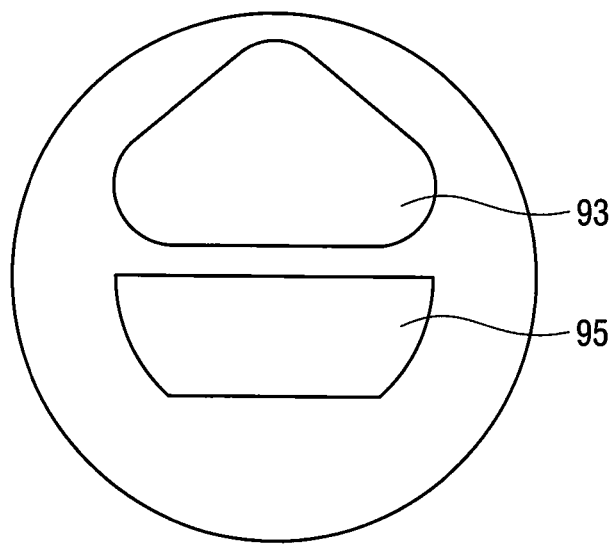
FIG. 3B is a transverse cross-sectional view of the catheter of FIG. 3A.
Figure 4A:
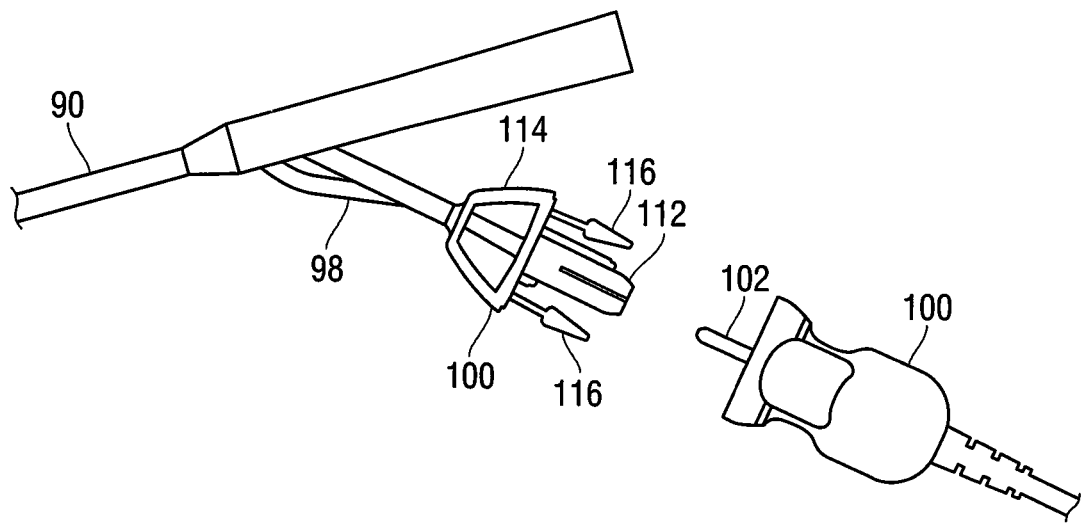
FIG. 4A is a perspective view of the proximal end of the catheter of FIG. 3A and the transducer hub prior to attachment to the catheter.
Figure 4B:
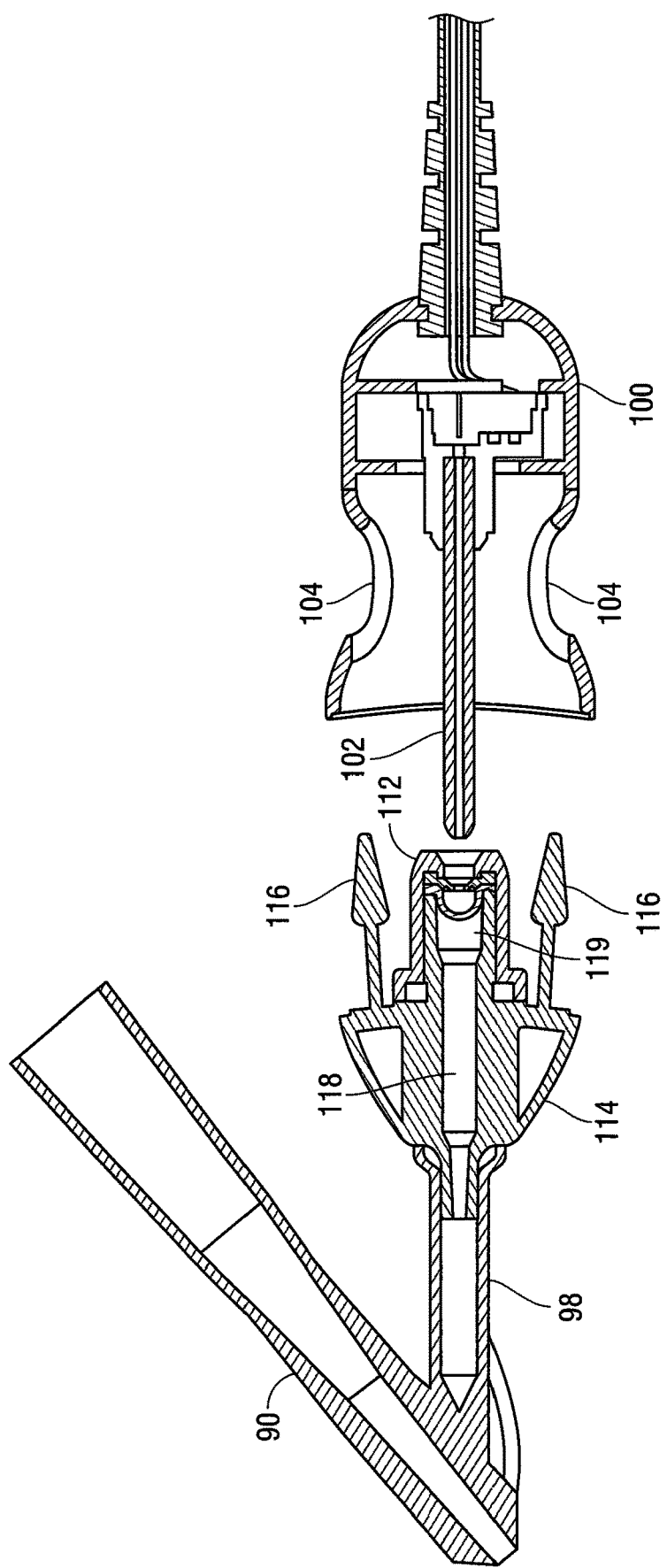
FIGS. 4B and 4C are cutaway side views showing the pressure transducer hub of FIG. 4A prior to connection to the catheter of FIG. 3A, a portion of the hub wall and catheter connector removed to show internal components.
Figure 4C:
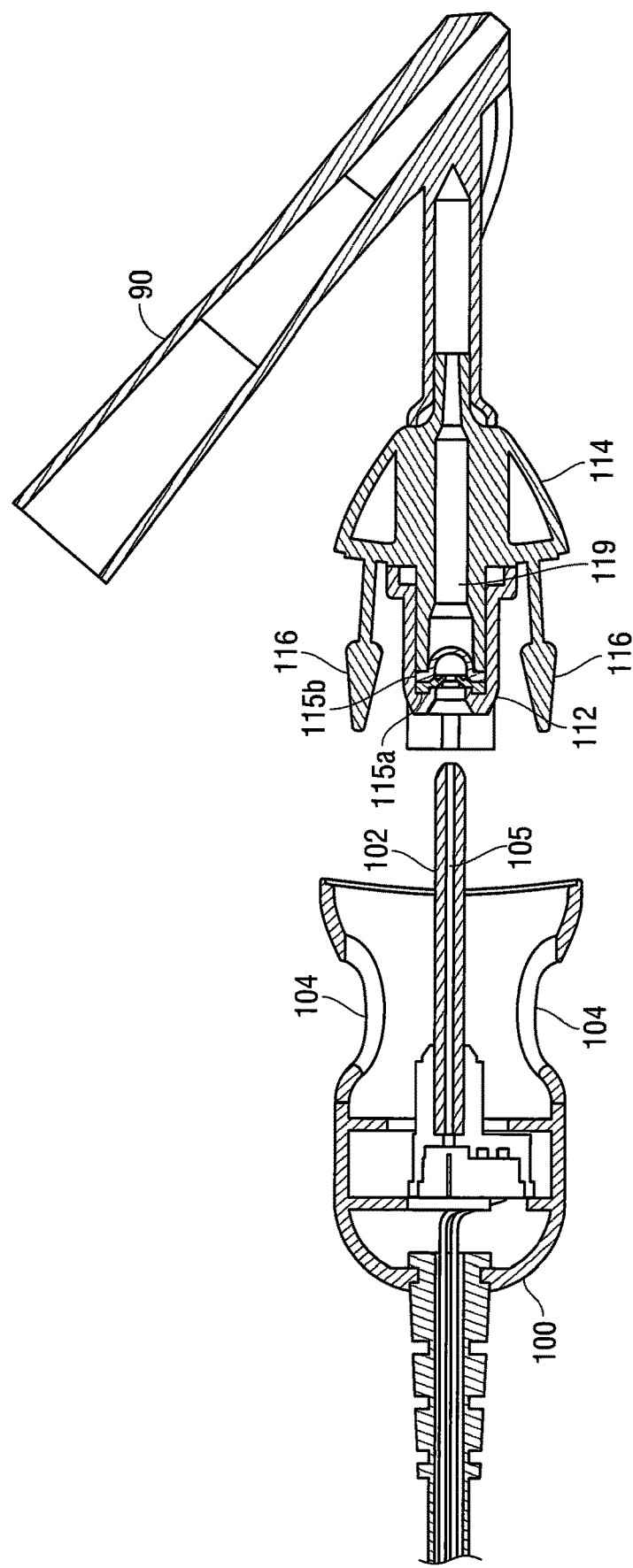
Figure 5:
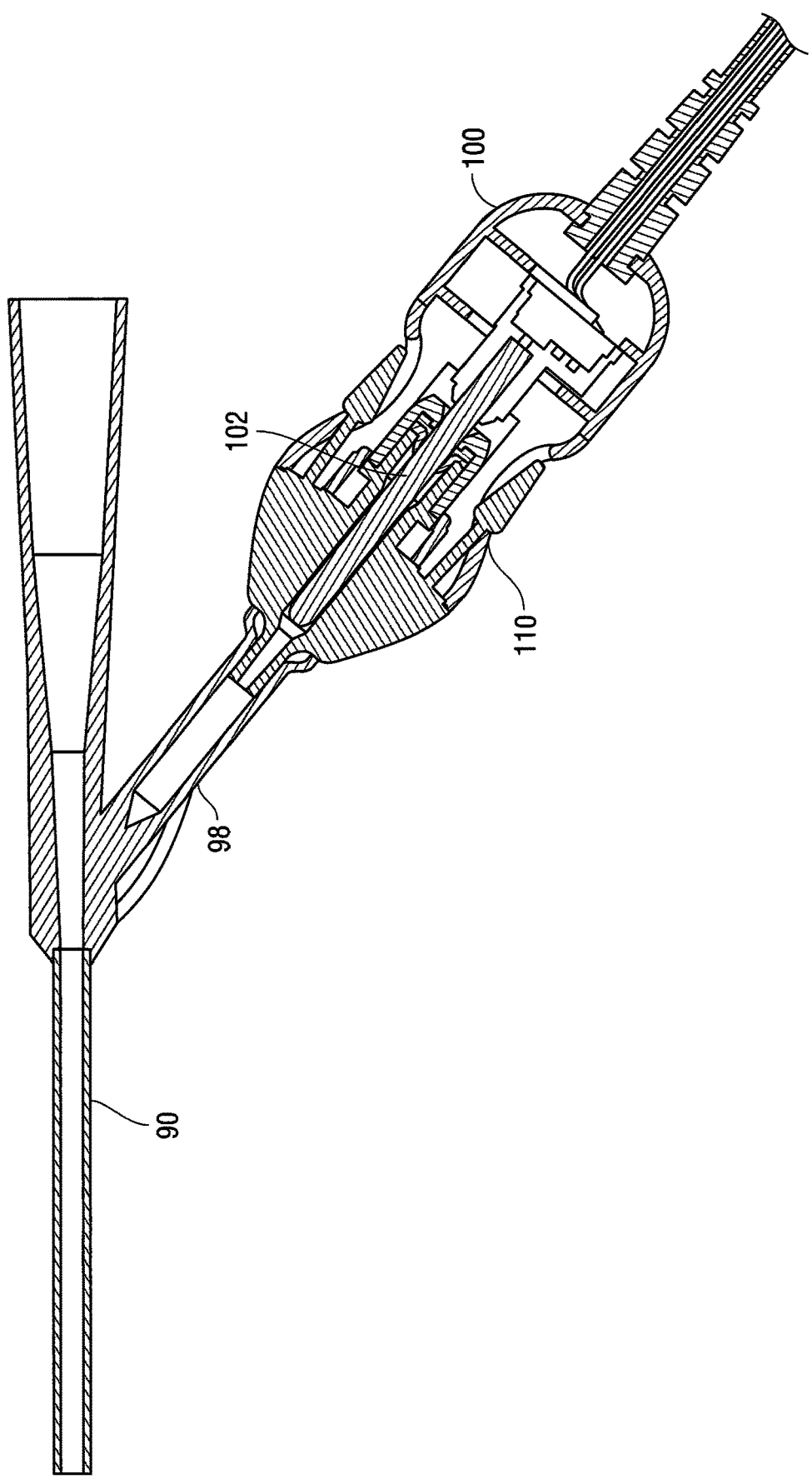
FIG. 5 is a side view showing the transducer hub of FIG. 4A attached to the catheter of FIG. 3A.

As shown in the cross-sectional view of FIG. 3B, the catheter 90 has a lumen 93 communicating with the pressure balloon. Another lumen 95 could be provided for another sensor (e.g., for measuring oxygen saturation) or for injection of fluids. The cross-sectional shape and size of the lumens is shown by way of example as other shapes and sizes of the lumens in this and the other embodiments disclosed herein are also contemplated.

Figure 6A:
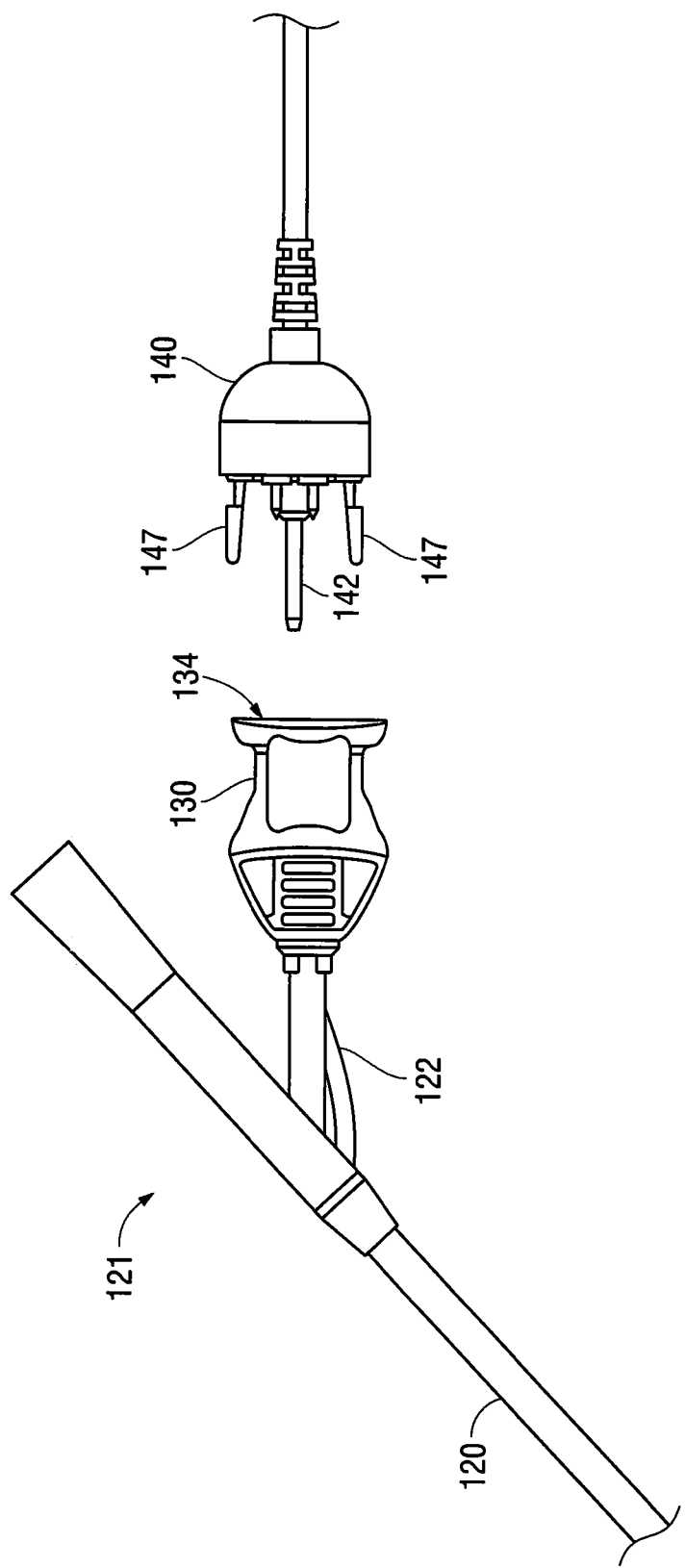
FIG. 6A is a perspective view of an alternate embodiment of the pressure transducer hub and connector prior to attachment of the hub to the catheter.
Figure 6B:
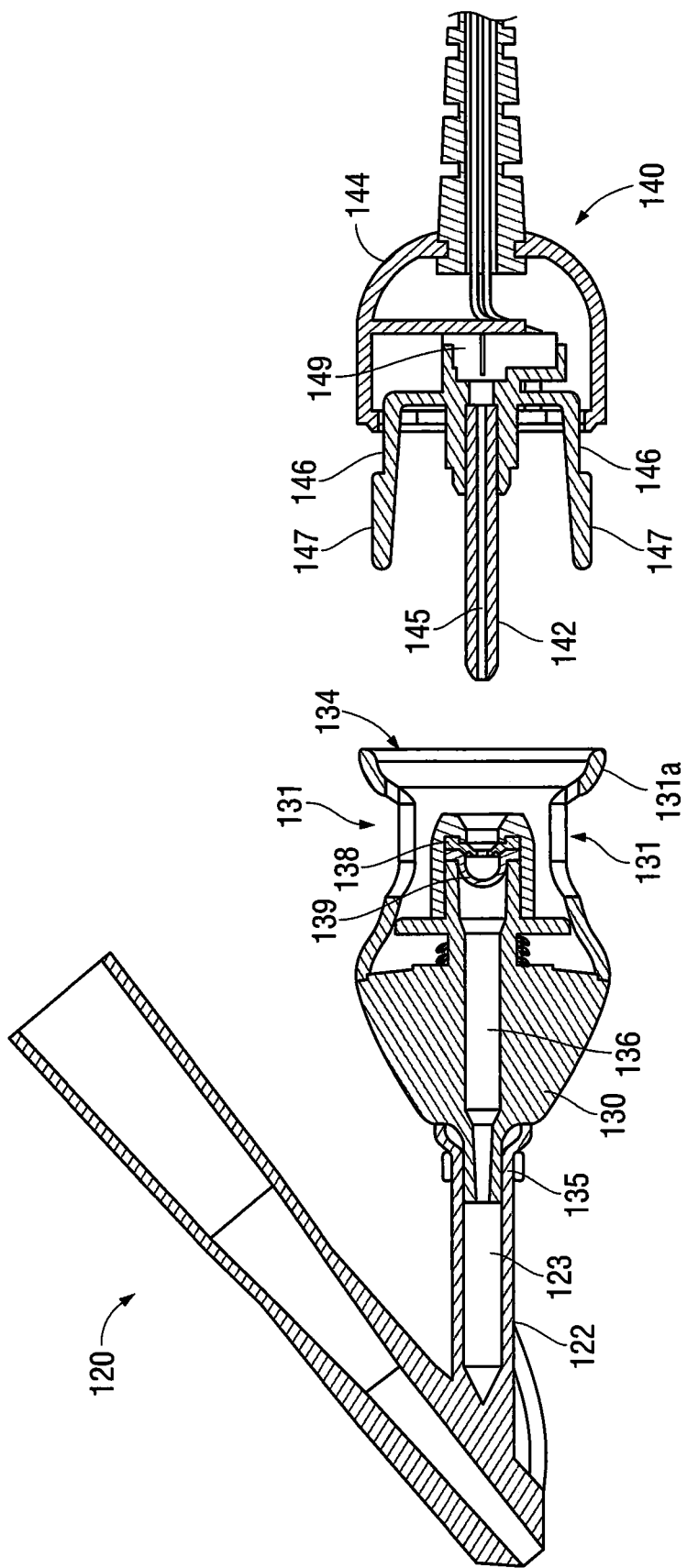
FIG. 6B is a cutaway side view of the hub and connector of FIG. 6A showing the hub prior to connection to the catheter of FIG. 6A, a portion of the hub wall and connector removed to show internal components.
Figure 6C:
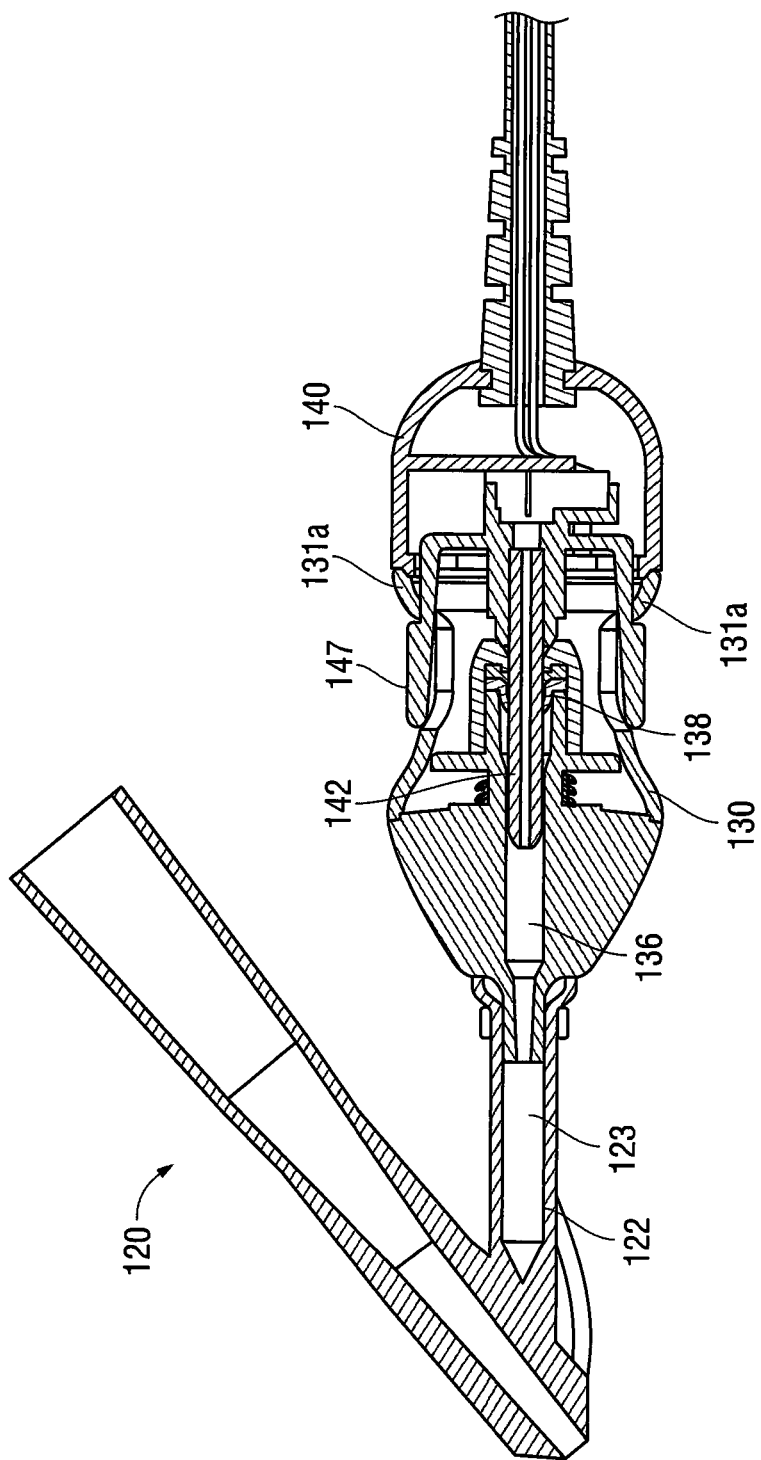
FIG. 6C is a cutaway side view similar to FIG. 6B showing the hub attached to the catheter.
Figure 6D:
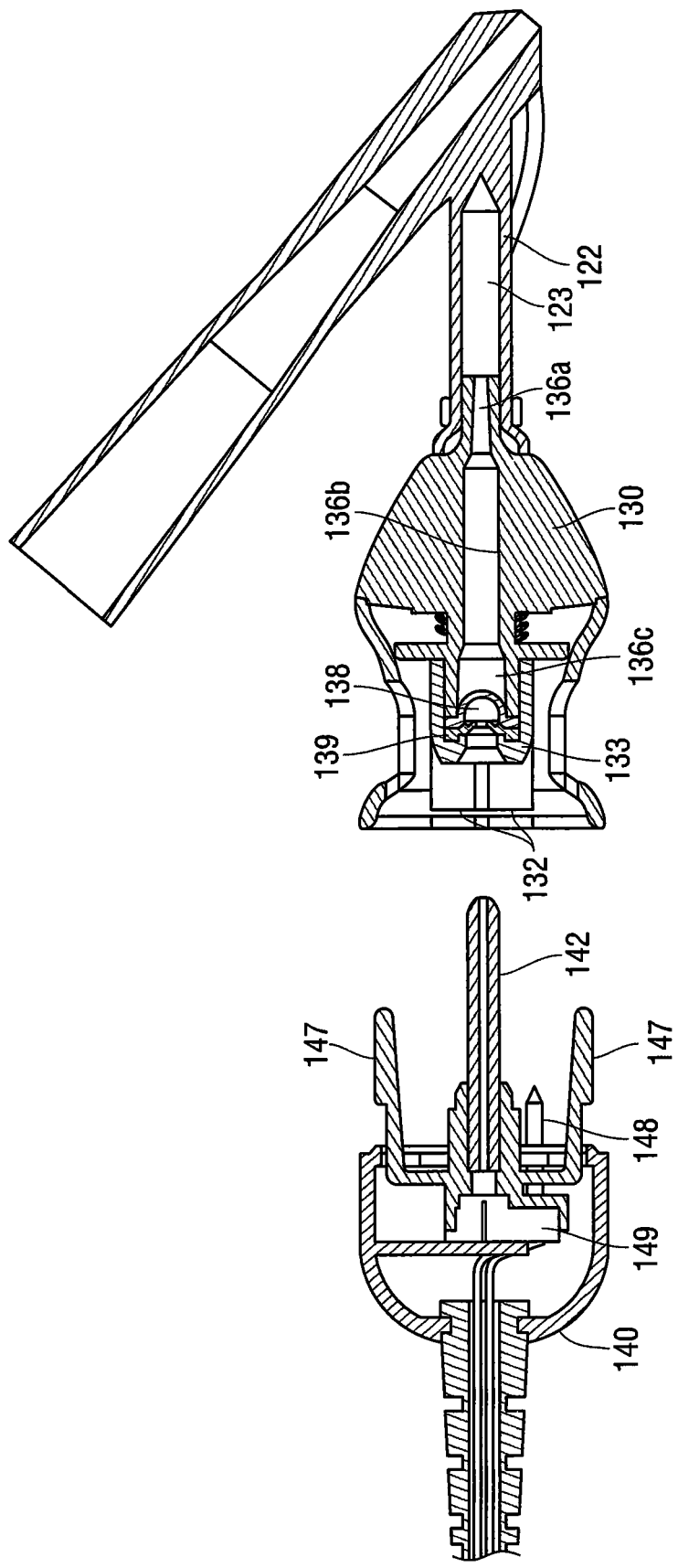
FIG. 6D is a cutaway side view similar to FIG. 6B from the other side.

The pressure transducer and pressure sensor are external to catheter 90 and mounted to port 98 at the proximal end 90a of catheter 90. More specifically, a transducer hub or housing, designated generally by reference numeral 100, contains the pressure transducer and sensor and is mounted to the angled side port 98. In the embodiment of FIG. 3A, the hub 100 is mounted over the port 98 and can be locked or secured thereto via connector 110 such as by a snap fit, although other attachments are also contemplated such as a friction fit, threaded attachment, a latch, etc. as well as other types of snap fits to provide an attachment that maintains an airtight seal so the air (or other gas) is contained within the air lumen and balloon 92. The hub 100 has an elongated (rod-like) member or nose 102 extending distally therefrom (FIG. 4A) for insertion through the extension 112 of connector 110. More specifically, connector 110 is mounted to side port 98 and has a distal housing 114 from which a pair of proximally extending snap fit connector arms 116 extend. The arms 116 are sufficiently flexible to enable attachment and have an enlarged proximal portion, illustratively shown as arrow shaped although other enlarged shapes could be provided. The distal housing 114 has a lumen 118 for communication with the lumen in the side port 98 of catheter 90. The lumen 118 also communicates with the lumen 119 in the proximal extension 112 dimensioned to receive the elongated rod 102 of transducer 100. The wire(s) for the sensor extends in housing 100. Recesses 104 in hub 100 are dimensioned to receive arms 116 when transducer hub 100 is attached to connector 110. Such attachment inserts the elongated rod 102 through seals into lumen 119 and 118 to advance air (or other gas) though the air lumen in the catheter and into the balloon 92. (Note the air lumen extends into its angled side port 98 communicating with the lumen extending longitudinally through the catheter). The elongated member 102 also has a channel 105 extending therethrough to allow the pressure wave to travel through to the pressure sensor. Although in preferred embodiments no additional air needs to be injected into balloon 92 after attachment of hub 100, it is also contemplated that a port or opening can be provided in hub 100 to receive an injection device for injection of additional air. Such additional air can communicate with and flow through channel 105 of elongated member 102, into the air lumen and balloon 92 for inflation, or alternatively, a side port or opening in the angled port downstream of the elongated member 102 could be provided for additional air injection. The lumen which is used to inflate the balloon 92 and create the air column has an opening at a distal region to communicate with the interior of inner balloon 92. Although the arms 116 are disclosed as extending proximally from the connector 110 to engage recesses 104 of transducer hub 100, it is also contemplated that alternatively, as shown in the embodiment of FIG. 6A discussed in detail below, the arms can be placed on the transducer hub 100 and the recesses to receive the arms placed on the connector to latch in the same manner as in the embodiment of FIG. 4A.

To charge the system, when the hub 100 is mounted to the side port 98 via attachment to connector 110, the elongated member 102 extends into lumens 119 and 118 to advance air (or other gas) through the air lumen into balloon 92 to expand the balloon 92. That is, connection of the transducer hub 100 to the catheter 90 (port 98) automatically advances air through the longitudinally extending lumen 96 to expand the balloon 92. In some embodiments, 0.2 cc of air can be displaced/advanced by the member 102, although other volumes are also contemplated. Thus, as can be appreciated, mounting of the hub 100 to the catheter 90 automatically pressurizes the air lumen/chamber and expands the balloon. Note the balloon can be partially or fully inflated (expanded), dependent on the amount of air advanced into the balloon. Further note that the lumen is not vented to atmosphere when the transducer hub 100 is attached and air is advanced through the air lumen. The port 98 or connector 110 can include a closable seal through which the elongated member 102 is inserted but maintains the seal when the elongated member 102 remains in the lumen 104. The seal can be provided near the entry of the elongated member 102 as in the dome shaped seal (valve) 115b and seal (valve) 115a.

Note as in other embodiments disclosed herein, air is described as the preferred gas for creating the column and expanding the balloon, however, other gasses are also contemplated.

The balloons of the embodiments disclosed herein can be symmetrically shaped as shown or alternatively asymmetrically shaped such that for example a distal region has an outer transverse cross-sectional dimension, e.g., diameter, greater than an outer transverse cross-sectional dimension, e.g., diameter, of the proximal region. A smooth transition (taper) can be provided between the distal region and proximal region, although other configurations are also contemplated. The balloon can by way of example be made of urethane, although other materials are also contemplated.

In the illustrated embodiment of FIG. 3A, the wire connector can plug into the openings of a connector positioned on or in the hub 100. The wire connector can be internal of the hub with an opening in the wall of the hub to enable access for the wire connector. Also note that alternatively the wire can include a female connector and the hub can have a male connector. Other types of connectors/connections are also contemplated.

Wires can exit from the air lumen of catheter 90 for connection to an external pressure monitor via hub 100. The catheter 90, as in the foregoing embodiments, can have an atraumatic tip 90b.

In use, catheter 90 is inserted into the muscle compartment and the system is charged by inflation of the balloon 92, preferably partially inflated for the reasons discussed above, by advancement of air through the air lumen upon attachment of the pressure transducer 100 to the connector 110 of port 98 of catheter 90. Such attachment moves elongated member 102 into the lumen 93 in connector 110 to displace the air already in the lumen to expand the balloon 92. A closed system is formed by the internal space of the balloon 92 and the internal lumen communicating with the internal space of balloon 92. In a preferred embodiment, additional air does not need to be added to the balloon 92/lumen 93. With the balloon 92 inflated, pressure monitoring can commence as external pressure applied to the balloon 92 compresses and deforms the balloon based on changes to compartment pressure, and the pressure sensor within the external hub 100 attached at the proximal end of the catheter 90 provides pressure readings, preferably continuously, converted to an electrical signal by the transducer within the hub 100, and then electrically communicates through a connector, e.g., cable 105, to an external monitor either directly or via a converter to display pressure readings. Although, the system is capable of continuous pressure monitoring, it can also be adapted if desired for periodic monitoring so the pressure readings can be taken at intervals or on demand by the clinician. As noted above, preferably no additional air needs to be added after mounting of hub 100. However, it is also contemplated that in alternate embodiments a port can be provided in communication with hub 100 to enable subsequent injection of air through the lumen 96 and into balloon 92.

FIGS. 6A-6D show an alternate embodiment of the hub/connector. The pressure transducer is external to catheter 120 and mounted to port 122 at the proximal end 121 of catheter 120 via connector (housing) 130. Catheter 120 is identical to catheter 90 of FIG. 3A except for the connector and transducer hub connection.

More specifically, transducer hub or housing, designated generally by reference numeral 140, contains the pressure transducer and sensor 149 and is mounted to the angled side port 122. In the embodiment of FIG. 6A, the hub 140 is mounted to the catheter 120 by connection to housing 130. Housing 130 is connected to port 122 via a barbed fitting 135 providing an interference fit with the port 122. The hub 140 is locked or secured to connector 130 such as by a snap fit provided by the latch arms discussed below, although other attachments are also contemplated such as a friction fit, threaded attachment, other form of latch, etc., as well as other types of snap fits to provide an attachment that maintains an airtight seal so the air is contained within the air lumen and balloon of the catheter 120. As noted above, catheter 120 is identical to catheter 90 except for its connector so catheter 120 includes a pressure balloon, etc.

The housing (connector) 130 attached to catheter 120 has a proximal opening 134 and a channel (lumen) 136 to receive an elongated (rod-like) member or nose 142 extending distally from transducer hub 140. As shown channel 136 has a first diameter region 136a to match with the lumen 123 of the port 122, a second larger diameter region 126b proximal of region 126a to receive the male rod 142 of the hub 140, and a still larger diameter region 136c proximal of region 136b to receive the valve 139 and valve 138 and allow expansion thereof. As shown, valve 138 is dome shaped and is distal of valve 139. Conical cap 133, proximal of valve 139, provides a lead in to the valve 139 for the rod 142. Note valves 138, 139 are one example of valves that can be provided as other valves to provide an airtight seal are also contemplated. A single valve is also contemplated.

Hub 140 is mounted to connector 130 and includes a housing 144 from which a pair of distally extending snap fit connector arms 146 extend. The latch arms 146 are sufficiently flexible to enable attachment and have an enlarged distal portion 147, illustratively shown as arrow shaped although other enlarged shapes could be provided. The elongated member 142 extends between the latch arms 146. When the hub 140 is mounted to the connector 130, the elongated member 142 extends into the channel 136 to advance air to inflate the inner balloon. The enlarged ends 147 of latch arms 146 enter recesses 131 and engage shoulders 131a to retain the hub 140. Note to release (disconnect) the hub 140, the ends 147 are pressed radially inwardly to disengage from shoulder 131a and the hub 140 is pulled proximally. Note that alternatively a different number of latch arms could be provided.

The housing (connector) 130 has a lumen 136 for communication with the lumen 123 in the side port 122 of catheter 120 which communicates with the air lumen and pressure balloon of the catheter 120. As noted above, the lumen 136 is dimensioned to receive the elongated rod 142 of transducer hub 140. The wire for the sensor extends in housing 140. When transducer hub 140 is attached to connector 130, such attachment inserts the elongated rod 142 into lumen 136 to advance air though the air lumen in the catheter and into the pressure balloon. (Note the air lumen extends into its angled side port 122). The elongated member 142 also has a channel or lumen 145 extending therethrough to allow the pressure wave to travel through to the pressure sensor. Although in preferred embodiments no additional air needs to be injected into the pressure balloon after attachment of hub 140, it is also contemplated that a port or opening can be provided in hub 140 to receive an injection device for injection of additional air. Such additional air can communicate with and flow through channel 145 of elongated member 142, into the air lumen and balloon for inflation, or alternatively, a side port or opening in the angled port downstream (distal) of the elongated member 142 could be provided.

In certain embodiments where a temperature sensor is provided, attachment of hub 140 to housing 130 also automatically connects thermistor connectors 148 to thermistor pins 132 to automatically connect the temperature sensor to the hub 140 for communication via a cable to a temperature monitor.

To charge the system, when the hub 140 is mounted to the side port 122 via attachment to connector 130, the elongated member 142 extends into lumen 136 to advance air through the air lumen into the pressure balloon to expand the balloon. That is, connection of the transducer hub 140 to the catheter 120 (port 122) automatically advances air through the connector lumen 136, the port lumen 123 and the first lumen of the catheter 120 to expand the balloon. In some embodiments, 0.2 cc of air can be displaced/advanced by the member 102, although other volumes are also contemplated. Thus, as can be appreciated, mounting of the hub 140 to the catheter 120 automatically pressurizes the air lumen/chamber and expands the balloon. Note the balloon can be partially or fully inflated (expanded), dependent on the amount of air advanced into the balloon. Further note that preferably the lumen is not vented to atmosphere when the transducer hub 140 is attached and air is advanced through the air lumen. The port 122 includes a closable seal, e.g., valves 138 and 139, through which the elongated member 142 is inserted but maintains the seal when the elongated member 142 remains in the lumen 136. Note that catheter 120 is identical in all other respects to catheter 90 so that the description of catheter 90 and its components and function (and alternatives) are fully applicable to catheter 120, the difference being the connector 130 of catheter 90 to receive transducer hub 140. The transducer hub is also different, e.g., has latch arms and a different configuration.

In alternate embodiments, any of the catheters disclosed herein can include a channel (lumen) for sensors for measuring different parameters and their associated wires (unless wireless) can be provided in separate channels, or alternatively, one or more sensors and their associated wires can be provided in a single channel to reduce the overall size/diameter of the catheter.

Figure 8A:
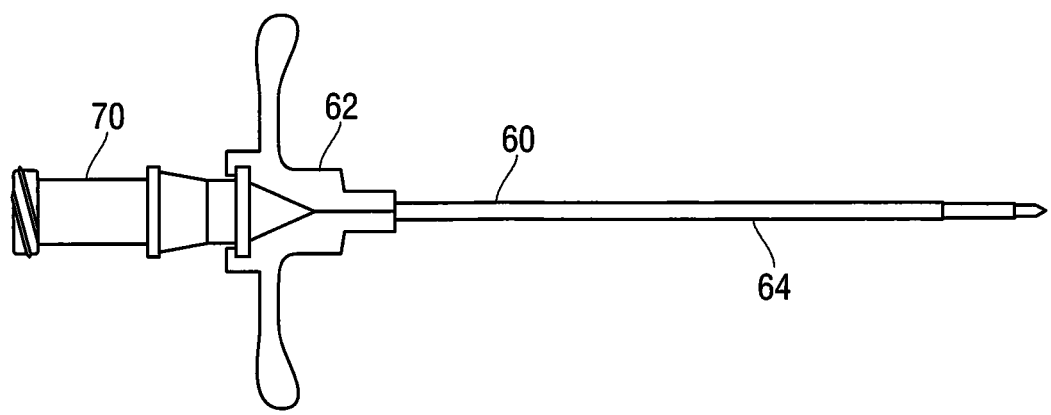
Figure 8B:
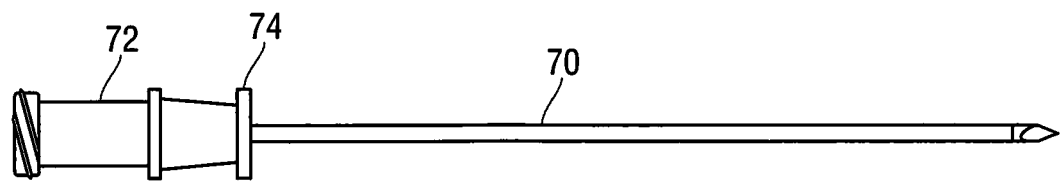
Figure 8C:
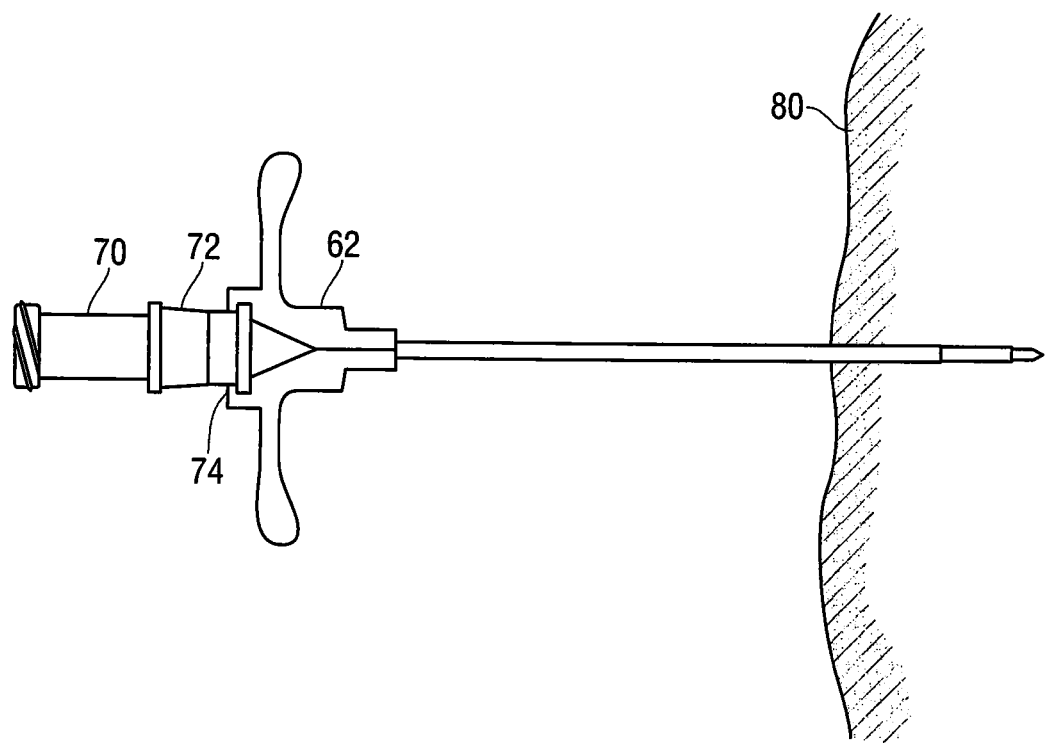
Figure 8D:
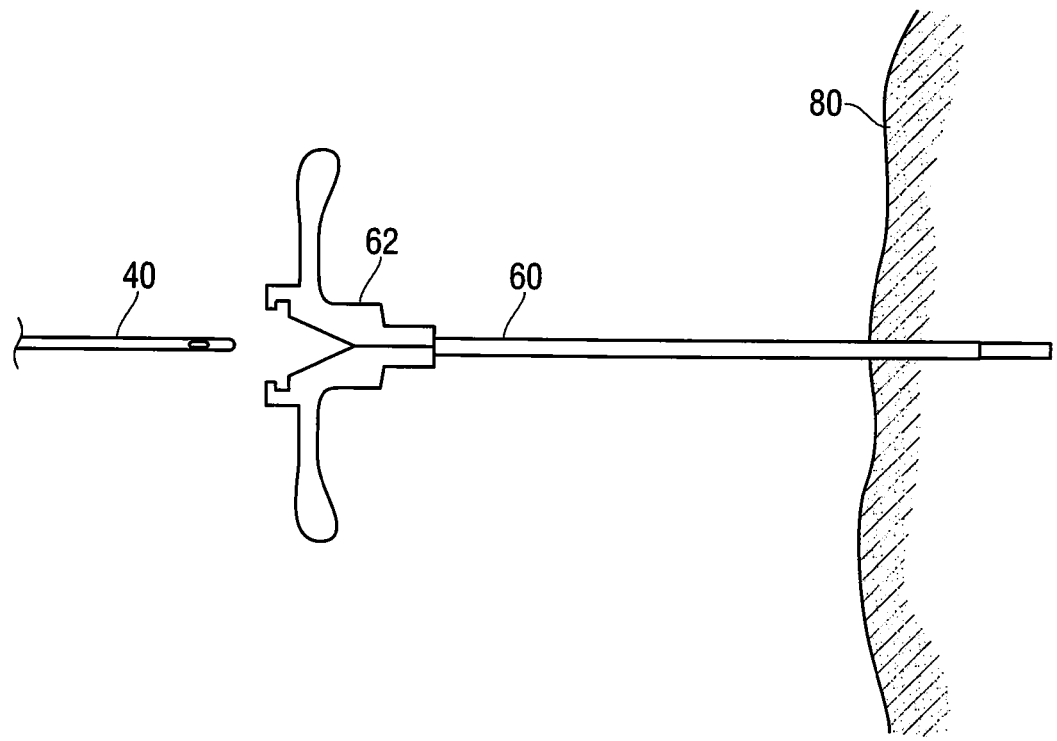
Figure 8E:
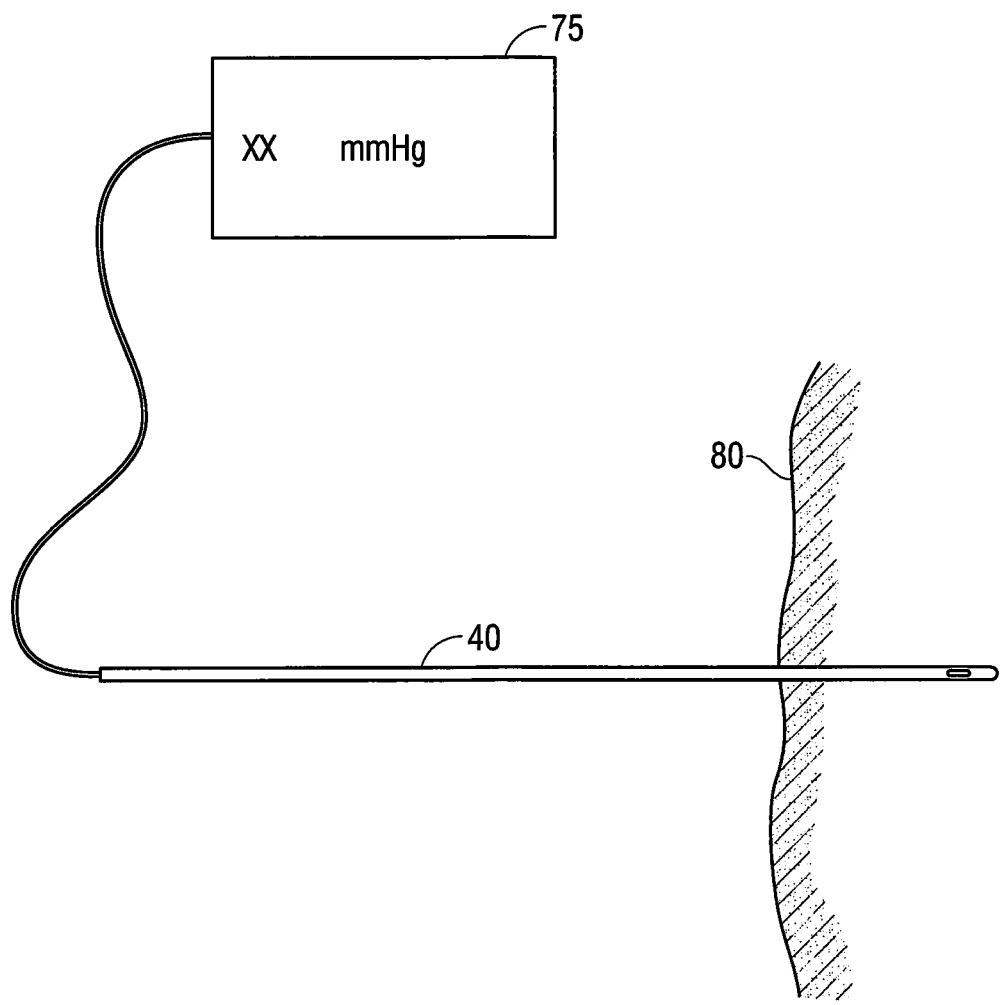

The catheters disclosed herein in some embodiments can be inserted through a sheath as shown in FIGS. 8A-8E. The sheath 60 has a hub 62 and a lumen extending through shaft 64, extending distally from the hub 62 and terminating in a distal opening. A needle 70 with a sharpened tip, is first inserted though the sheath 60 (FIG. 8A), and its flange 74 on handle 72 engages, e.g., snaps into, hub 62 of sheath 60 and together they are inserted through tissue 80 into the muscle compartment (FIG. 8C). After insertion into the muscle compartment, the needle 70 is withdrawn, leaving sheath 60 in position for insertion of one of the catheters of the present invention disclosed herein. Catheter 40 is shown in FIG. 8D by way of example, and it should be understood that the other catheters described herein can be inserted through the sheath 60. After insertion of the catheter, the sheath 60 is removed from the body. In some embodiments, the sheath 60 is a peel away sheath which can be removed by separating the sheath at the wings of the hub 62 to separate the sheath along its length so it can be pulled from the body without effecting placement of the catheter. After removal of the sheath, the catheter is then connected to pressure monitor 75 as shown in FIG. 8E to provide readouts of pressure measurements within the muscle compartment. To reduce the outer diameter of the device, a guidewire like device or hypotube having a microtip sensor can be used instead of the catheter and inserted through the sheath 60 in the same manner as the catheter. Alternatively, a guidewire like device with a sensor can be inserted through the catheter.

As noted above, the catheters of the present invention can alternatively be inserted without a sheath. For example, the physician can use this unsheathed version to take a pressure reading in the already surgically-opened muscle/fascial tunnel, e.g., the passageway connecting the forearm to the hand (the carpal tunnel), and only perform further surgery if tunnel pressure is elevated. The catheter will thus eliminate the risks of performing unnecessary carpal tunnel surgery by detecting whether pressure in the tunnel is elevated before carpal tunnel release surgery is initiated. For example, a 3 French air charged balloon catheter can in some embodiments be inserted into the carpal tunnel area, e.g., slid over a needle, to assess tunnel pressure to determine if carpal tunnel surgery is indicated/warranted. It is also contemplated that the sheathed version can be used for insertion into the carpal tunnel to detect pressure.

In some embodiments, the placement of the catheters into the carpal tunnel or other areas of the body can be guided by ultrasound.

Another example of use of an unsheathed version of the catheters of the present invention (although a sheathed version could also be utilized) is measuring pressure in the sub-occipital muscles located at the top of the spine to help determine whether a patient is suffering from occipital neuralgia (pain in the occipital nerves) or migraine due to other factors. The cause of occipital neuralgia is unknown but compression of the occipital nerves by arteries or tumors is one of several hypotheses. By taking a pressure reading in the already surgically opened muscle tunnel, it can be determined to continue surgery only if pressure in the tunnel is elevated, thereby eliminating the risks of performing unnecessary surgery.

As noted above, the catheters of the present invention can also be used by military organizations to monitor combat wounds to determine if fasciotomy is indicated.

Figure 9A:
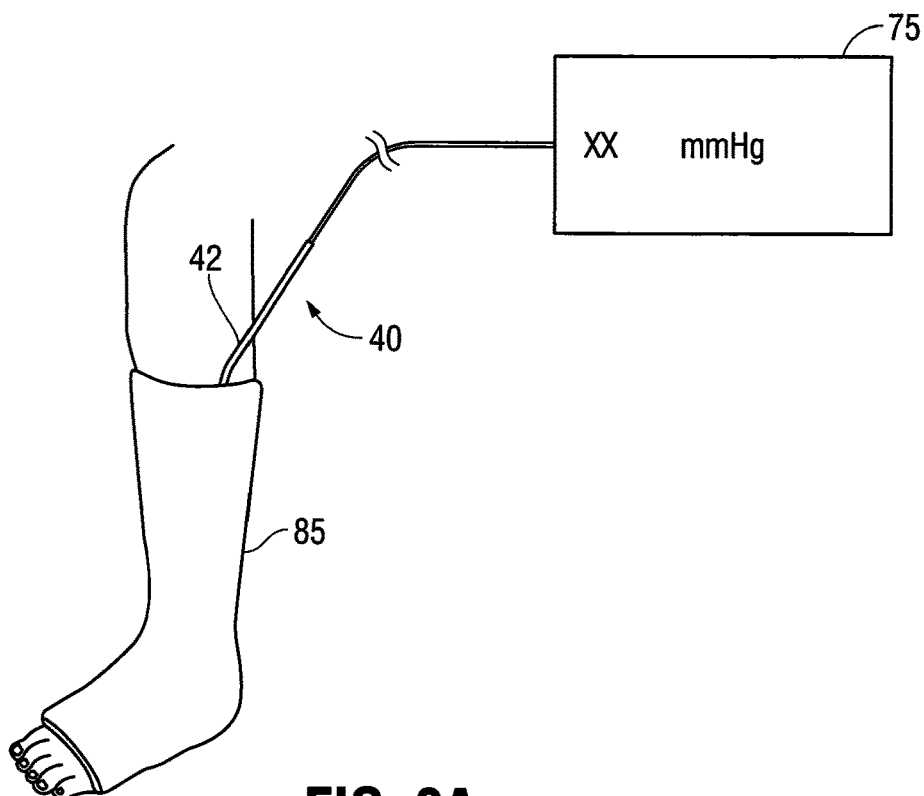
FIG. 9A illustrates the catheter of FIG. 2 positioned within an orthopedic cast.

As noted above, the catheters of the present invention can be left in the body for an extended period of time, e.g., several weeks. In some embodiments, as noted above, the catheters of the present invention can be used with orthopedic casting. The catheters of the present invention in certain embodiments can be set in place before casting, and reside within the cast for an extended period of time (e.g., several weeks) to monitor for pressure increases that present a risk of damage or death to muscle and nerves. They can be further held by tape, e.g., taped to the skin of the patient. Placement within a cast is shown for example in FIG. 9A wherein at least a distal portion of the catheter is positioned within the foot cast 85, with a proximal end 42 exposed from the cast 85 for connection to a pressure monitor 75. In this manner, intramuscular pressure can be continuously or intermittently monitored without removing the cast to monitor pressure increases that present a risk of damage or death to the muscles and nerves. Without such monitoring by the externally extending catheters, if symptoms arise, the cast would need to be removed which is not only time consuming and expensive, but in certain instances could be too late to prevent serious damage/effects. By monitoring within the cast, problems can be detected at an early more-treatable stage.

Pulse-oximeter readings can in some embodiments be provided at the same time as pressure readings to determine when to appropriately surgically intervene. Sensors to provide such readings can be provided with any of the catheters and any of the clinical applications disclosed herein.

Figure 9B:
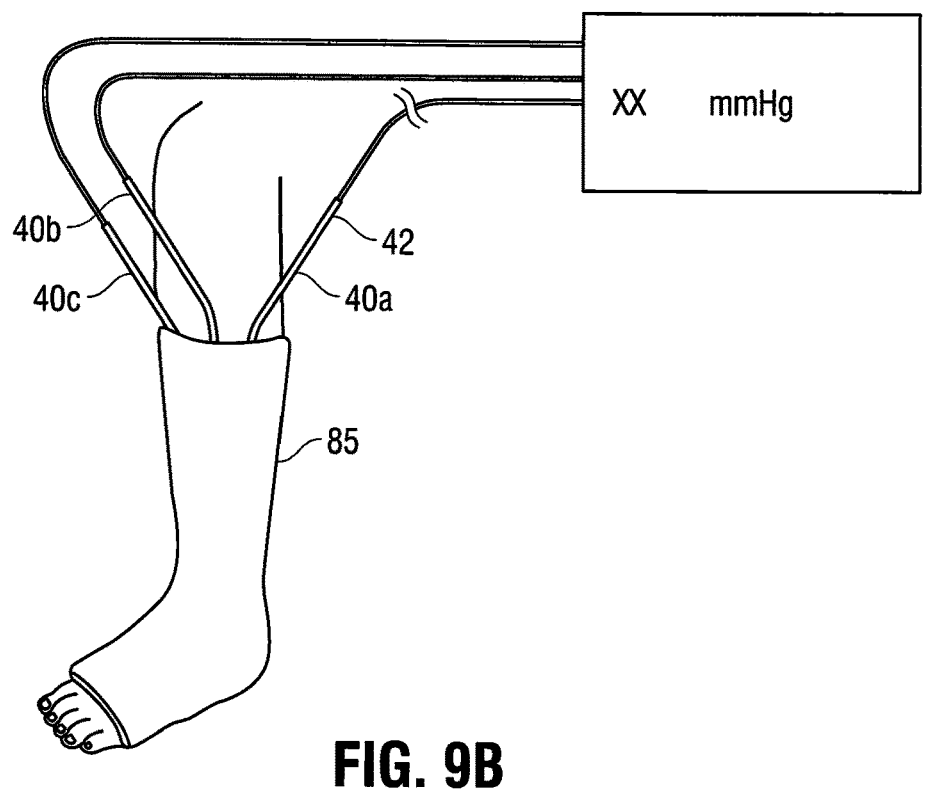
FIG. 9B illustrates multiple pressure sensing catheters positioned in the orthopedic cast and connected to a common external monitor.

In some embodiments the device for placement within the orthopedic cast comprises a micro-tip sensor at the end of a hypotube, with the wires extending though the lumen in the hypotube. The hypotube can be made of Nitinol (nickel-titanium alloy) which reduces kinking and breaking of the hypotube extending from the cast. Other materials such as a braided shaft or polymeric materials can alternatively be utilized provided such materials minimize the chances of kinking and breaking during movement. The hypotubes can be of various lengths. Additionally, several hypotubes with micro-tip sensors can be placed within the cast to monitor multiple muscles. These multiple sensor/hypotubes can be connected to separate monitors or alternatively to a common monitor to provide readouts of the pressure from the multiple muscles. An example of such multiple hypotubes is illustrated in FIG. 9B, with hypotubes 40a, 40b and 40c extending from cast 85 and electrically connected to a common monitor 75.

In some embodiments, a porous material can be placed over the sensor.

An antimicrobial agent can be provided over portions of the catheter to prevent infection if the catheter is being placed in the body for an extended period of time.

The pressure balloon can be coated in some embodiments to prevent diffusion if the catheter is being placed in the body for a period of time.

The catheters can also in some embodiments monitor several muscles at a time.

The catheters of preferred embodiments of the present invention enable the patient to ambulate while pressure is being monitored. Since pressure changes when a patient moves from a sitting or lying position to a standing position, pressure in such embodiments can be monitored in all positions.

As noted above, hard wired or wireless connections of the sensor/catheter to the pressure monitor are contemplated.

It is also contemplated that a backup system can in some embodiments be provided to determine pressure. The backup system can provide a double check of pressure readings to enhance accuracy. Such backup system can be used with any of the embodiments disclosed herein to provide a second pressure reading system. One example of such backup system has a pressure transducer/pressure sensor like sensor 30 of FIG. 1C within the air lumen communicating with the pressure balloon (or alternatively a micro-tip sensor) forming a "first system", plus a pressure transducer/pressure sensor at a proximal end of the catheter or external of the catheter forming a "second system". Thus, a pressure sensor is at a distal end of the air charged lumen and a pressure sensor is at proximal end of the air charged lumen. Both sensors are electrically connected to a monitor that provides a graphic display of pressure readings. In such embodiments, with the balloon inflated, pressure monitoring can commence as external pressure applied to an outer surface of the balloon compresses the gas within the chamber. The sensor at the distal end of the lumen provides continuous pressure readings, converted to an electrical signal by the transducer within the distal end of the lumen, and then electrically communicates through its transmission wires extending through the air lumen to an external monitor either directly or via a converter. Additionally, pressure within the air charged column is measured at a proximal region by a sensor within a side port or proximal end of the longitudinally extending lumen of the catheter. The sensor at the distal end of the lumen provides pressure readings, and such pressure readings can be confirmed by the proximal sensor. Such pressure readings can be performed continuously or alternatively can also be adapted if desired for periodic monitoring so the pressure readings can be taken at intervals or on demand by the clinician. Thus, air pressure readings at a proximal end plus pressure readings at the distal end are provided. The sensors can electrically communicate with an external monitor to display both pressure readings from the sensors, or alternatively, if the pressure readings are different, they can be averaged to display a single measurement. Clearly, other displays of information can be provided to display the information from the two sensors.

The sensors disclosed herein can also be microtip sensors within the shaft lumen at a distal end. In alternative embodiments, fiber optic sensors within the lumen can be utilized to measure pressure exerted on the muscle compartment. The pressure transducers can be housed within the catheter or alternatively external to the catheter.

As discussed above, the catheters provide a closed system. The catheters with a balloon provide a large reservoir (large capacity) and large circumferential area/interface for obtaining more information from the muscle compartment over multiple reference points (rather than a single point sensor) that provides an average pressure to provide a gross measurement and assessment of the surrounding environment as pressure measurement is not limited to one side of the compartment but can determine measurements on the opposing side.

As noted above, the catheters, i.e. the transducer, can be connected to a bedside monitor or a handheld monitor providing a portable readout through either a wire or bluetooth wireless connection. Such wireless connection would provide the patient the increased ability to ambulate. The monitor can be provided as a kit with one or more catheters.

The system can also include an indicator or alarm system to alert the staff at the site as well as remote staff through wired or wireless connections to an external apparatus, e.g., hand held phones or remote monitors. The indicator can be a visual indicator such as a light, LED, color change, etc.

Alternatively, or additionally, the indicator can be an audible indicator which emits some type of sound or alarm to alert the staff. The indicator can be separate from the catheter, associated with the monitor, at the proximal region of the catheter or at other portions of the catheter, e.g., at a distal end portion, where known imaging techniques would enable the user to discern when the indicator is turned on. It is also contemplated that in addition to providing an alert to the user, the pressure or other monitoring system can be tied into a system to directly control parameters so that if the pressure or other parameter is outside a desired range, appropriate steps can be taken. In such systems, one or more indicators can be provided on the proximal portion of the catheter, e.g., at a proximal end outside the patient's body, or separate from the catheter. The sensor(s) is in communication with the indicator(s), either via connecting wires extending through a lumen of the catheter or a wireless connection. The sensor(s) can be part of a system that includes a comparator so that a comparison of the measured pressure, or other parameter, to a predetermined value is performed and a signal is sent to the indicator to activate (actuate) the indicator if the measured pressure value or other value is exceeded, thereby alerting the clinician or staff that pressure or other parameters are outside desired ranges and a signal is also sent to a device or system to automatically actuate the device or system to make the necessary adjustments. If the measured value is below the threshold, the indicator is not activated.

Although the apparatus and methods of the subject invention have been described with respect to preferred embodiments, those skilled in the art will readily appreciate that changes and modifications may be made thereto without departing from the spirit and scope of the present invention as defined by the appended claims.

What is claimed is:

1. A multi-lumen catheter for monitoring intramuscular pressure comprising an elongated body configured and dimensioned for insertion into a compartment of a patient, the catheter having a lumen and a balloon at a distal portion, the lumen communicating with the balloon, the balloon containing a gas to form along with the lumen a gas containing chamber to monitor intramuscular pressure to thereby determine if excessive pressure is being applied to determine muscle conditions of a patient to determine if steps need to be taken to relieve muscle pressure, wherein pressure is measured about a circumferential area of the balloon to provide readings of intramuscular pressure, wherein the balloon is expanded automatically upon connection to the catheter of a hub containing a sensor and a monitor connector, wherein automatic expansion is effected by an elongated rod displacing gas in the lumen upon connection of the hub to the catheter.

2. The catheter of claim 1, wherein the gas containing chamber is a closed system.

3. The catheter of claim 1, wherein the sensor is positioned adjacent the balloon.

4. The catheter of claim 1, wherein the sensor is positioned at a proximal region of the catheter.

5. The catheter of claim 1, wherein the balloon has a circumference engageable with the compartment at multiple contact regions to provide multiple reference points for calculation of an average pressure of the compartment.

6. The catheter of claim 1, wherein pressure is measured by a sensor which continuously measures pressure and continuously communicates with an external monitor to visually display pressure readings to assess if excess pressure is being exerted.

7. The catheter of claim 1, wherein the chamber contains air and after initial insertion of air to expand the balloon, additional air does not need to be inserted during the duration of insertion of the catheter in the patient.

8. The catheter of claim 1, wherein the catheter is configured for insertion into an introducer sheath.

9. The catheter of claim 1, further comprising at least one wire extending from the sensor through the lumen for connection to a cable, the cable in electrical communication with a pressure monitor positioned external of the catheter.

10. The catheter of claim 1, wherein a least a distal portion of the catheter is configured for implantation within an orthopedic cast, the proximal portion remaining exposed from the cast for connection to a pressure monitor without removing the cast.

11. The catheter of claim 1, further comprising an external pressure transducer connectable to the catheter and communicating with the gas containing chamber for measuring intramuscular pressure based on gas compression caused by deformation of the balloon.

12. The catheter of claim 11, wherein the pressure transducer is contained within the hub, and the elongated rod has a channel extending therethrough to allow a pressure wave to travel therethrough.

13. The catheter of claim 12, wherein the lumen is not vented to atmosphere when the pressure transducer is connected to the catheter and the elongated rod advances air to expand the balloon, and the catheter has a valve and the elongated rod is insertable through the valve when the hub is connected to the catheter.

14. The catheter of claim 12, wherein the chamber contains air and after initial advancement of air into the lumen by the elongated rod upon connection of the pressure transducer, additional air does not need to be inserted during the duration of insertion of the catheter in a body of a patient.

15. The catheter of claim 10, further comprising a second pressure monitoring catheter positioned within the orthopedic cast.

16. The catheter of claim 1, wherein the balloon includes an impermeable coating to prevent escape of gas from the balloon.

17. The catheter of claim 1, wherein the balloon is made of an impermeable material to prevent escape of gas from the balloon.

18. The catheter of claim 1, wherein the balloon is partially inflated during pressure measurement to provide compliancy of the balloon.

19. The catheter of claim 1, wherein the catheter is configured for insertion into a carpal tunnel and pressure is measured by a sensor to determine if tunnel pressure is elevated.

20. The catheter of claim 1, further comprising a pressure sensor, the pressure sensor measuring pressure in sub-occipital muscles to determine if pressure in a muscle tunnel is elevated.

* * * * *